United States Patent
Beckett et al.

(10) Patent No.: US 10,512,911 B1
(45) Date of Patent: Dec. 24, 2019

(54) IMPLEMENTING BARRIERS FOR CONTROLLED ENVIRONMENTS DURING SAMPLE PROCESSING AND DETECTION

(71) Applicant: Ultima Genomics, Inc., Newark, CA (US)

(72) Inventors: Nathan Beckett, Oakland, CA (US); Nathan Caswell, Sunnyvale, CA (US)

(73) Assignee: ULTIMA GENOMICS, INC., Newark, CA (US)

( * ) Notice: Subject to any disclaimer, the term of this patent is extended or adjusted under 35 U.S.C. 154(b) by 0 days.

(21) Appl. No.: 16/440,026

(22) Filed: Jun. 13, 2019

Related U.S. Application Data

(60) Provisional application No. 62/776,866, filed on Dec. 7, 2018.

(51) Int. Cl.
*B01L 3/00* (2006.01)
*G01N 7/02* (2006.01)
*G01N 33/487* (2006.01)

(52) U.S. Cl.
CPC ..... *B01L 3/50273* (2013.01); *B01L 3/502715* (2013.01); *B01L 3/502761* (2013.01); *G01N 7/02* (2013.01); *G01N 33/487* (2013.01); *B01L 2300/0877* (2013.01); *B01L 2300/14* (2013.01); *B01L 2400/049* (2013.01)

(58) Field of Classification Search
None
See application file for complete search history.

(56) References Cited

U.S. PATENT DOCUMENTS

| | | | |
|---|---|---|---|
| 4,611,881 A | 9/1986 | Schmidt et al. | |
| 5,216,247 A | 6/1993 | Wang et al. | |
| 5,409,811 A | 4/1995 | Tabor et al. | |
| 5,641,658 A | 6/1997 | Adams et al. | |
| 5,674,716 A | 10/1997 | Tabor et al. | |

(Continued)

FOREIGN PATENT DOCUMENTS

| | | |
|---|---|---|
| JP | 2000304688 A | 11/2000 |
| WO | WO-0039625 A2 | 7/2000 |

(Continued)

OTHER PUBLICATIONS

Adessi et al. Solid phase DNA amplification: Charcterisation of primer attachment and amplification mechanisms, Nucl. Acids Res, 2000, 28(20):E87.

(Continued)

*Primary Examiner* — Robert T. Crow
(74) *Attorney, Agent, or Firm* — Wilson, Sonsini, Goodrich & Rosati

(57) ABSTRACT

Provided herein are methods for processing and/or detecting a sample. A method can comprise providing a barrier between a first region and a second region, wherein the first region comprises the sample, wherein the barrier maintains the first region at a first atmosphere that is different than a second atmosphere of the second region, wherein a portion of the barrier comprises a fluid in coherent motion; and using a detector at least partially contained in the first region to detect one or more signals from the sample while the first region is maintained at the first atmosphere that is different than the second atmosphere of the second region. The portion of the barrier comprising fluid may have a pressure lower than the first atmosphere, the second atmosphere, or both.

30 Claims, 8 Drawing Sheets

(56) References Cited

U.S. PATENT DOCUMENTS

| | | |
|---|---|---|
| 6,737,238 B2 | 5/2004 | Suzuki et al. |
| 8,597,882 B2 | 12/2013 | Corbett et al. |
| 9,795,961 B1 | 10/2017 | Koh et al. |
| 9,891,177 B2 | 2/2018 | Vazhaeparambil et al. |
| 10,267,790 B1 | 4/2019 | Barbee et al. |
| 10,273,528 B1 | 4/2019 | Barbee et al. |
| 2002/0074517 A1 | 6/2002 | Krutchinsky et al. |
| 2003/0193589 A1 | 10/2003 | Lareau et al. |
| 2006/0078935 A1 | 4/2006 | Werner et al. |
| 2011/0178285 A1 | 7/2011 | Lebl et al. |
| 2012/0282708 A1 | 11/2012 | Corbett et al. |
| 2014/0162275 A1 | 6/2014 | Kotseroglou |
| 2015/0125346 A1 | 5/2015 | Schaff et al. |
| 2016/0032380 A1 | 2/2016 | Craighead et al. |
| 2016/0097727 A1 | 4/2016 | Vazhaeparambil et al. |
| 2016/0246170 A1 | 8/2016 | Bowen et al. |
| 2016/0319334 A1 | 11/2016 | Barany et al. |
| 2017/0136434 A1 | 5/2017 | Barnard et al. |
| 2018/0207920 A1 | 7/2018 | Venkatesan et al. |
| 2019/0153531 A1 | 5/2019 | Barbee et al. |

FOREIGN PATENT DOCUMENTS

| | | |
|---|---|---|
| WO | WO-0039625 A3 | 10/2000 |
| WO | WO-2019099886 | 5/2019 |

OTHER PUBLICATIONS

Bioptechs. Product information for the BIOPTECHS Objective Heather. Available at http://bioptechs.com/product/objective-heater/. Accessed on Jun. 25, 2019.

Brenner et al. In vitro cloning of complex mixtures of DNA on microbeads: Physical separation of differentially expressed cDNAs, Proc. Natl. Acad. Sci. USA 2000, 97(4):1665-1670.

Brenner, et al. Gene expression analysis by massively parallel signature sequencing (MPSS) on microbead arrays. Nat Biotechnol. Jun. 2000;18(6):630-4.

Co-pending U.S. Appl. No. 16/416,856, filed May 20, 2019.

Co-pending U.S. Appl. No. 16/416,889, filed May 20, 2019.

Co-pending U.S. Appl. No. 16/445,798, filed Jun. 19, 2019.

Dressman, et al. Transforming single DNA molecules into fluorescent magnetic particles for detection and enumeration of genetic variations. Proc Natl Acad Sci USA. 2003;100(15):8817-8822.

Lizardi, et al. Mutation detection and single-molecule counting using isothermal rolling-circle amplification. Nat Genet. Jul. 1998;19(3):225-32.

Mitra et al. Fluorescent in situ sequencing on polymerase colonies, Anal. Biochem, 320:55-65. (2003).

Mitra, et al. Digital genotyping and haplotyping with polymerase colonies. Proc Natl Acad Sci USA. 2003.100(10):15926-5931.

PCT/US18/61598 International Search Report and Written Opinion dated Mar. 15, 2019.

Pemov et al. DNA analysis with multiplex microarray-enhanced PCR, Nucl. Acids Res, 2005, 33(2):e11, pp. 1-9.

Reinartz, et al. Massively parallel signature sequencing (MPSS) as a tool for in-depth quantitative gene expression profiling in all organisms. Brief Funct Genomic Proteomic. Feb. 2002;1(1):95-104.

SPATIAL Transcriptomics. Workflow. Available at https://spatialtranscriptomics.com/workflow/. Accessed on Jun. 25, 2019.

Tabor, et al. Effect of manganese ions on the incorporation of dideoxynucleotides by bacteriophage T7 DNA polymerase and *Escherichia coli* DNA polymerase I, Proc. Natl. Acad. Sci. USA, Jun. 1989, 86:4076-80.

U.S. Appl. No. 15/974,364 Notice of Allowance dated Feb. 28, 2019.

U.S. Appl. No. 15/974,364 Office Action dated Aug. 7, 2018.

U.S. Appl. No. 15/974,441 Notice of Allowance dated Nov. 21, 2018.

U.S. Appl. No. 15/974,441 Office Action dated Aug. 3, 2018.

U.S. Appl. No. 15/974,543 Notice of Allowance dated Dec. 13, 2018.

U.S. Appl. No. 15/974,543 Office Action dated Aug. 7, 2018.

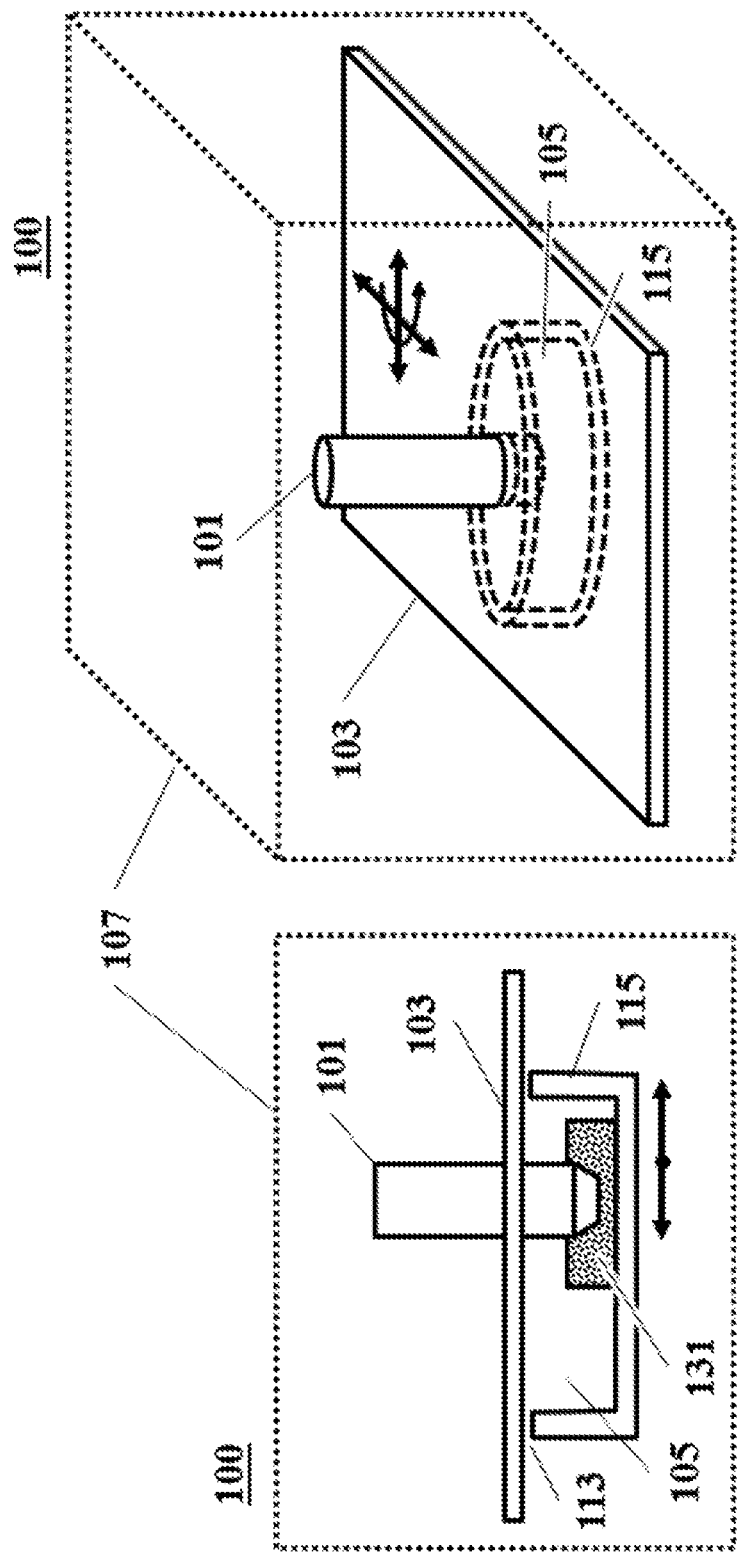

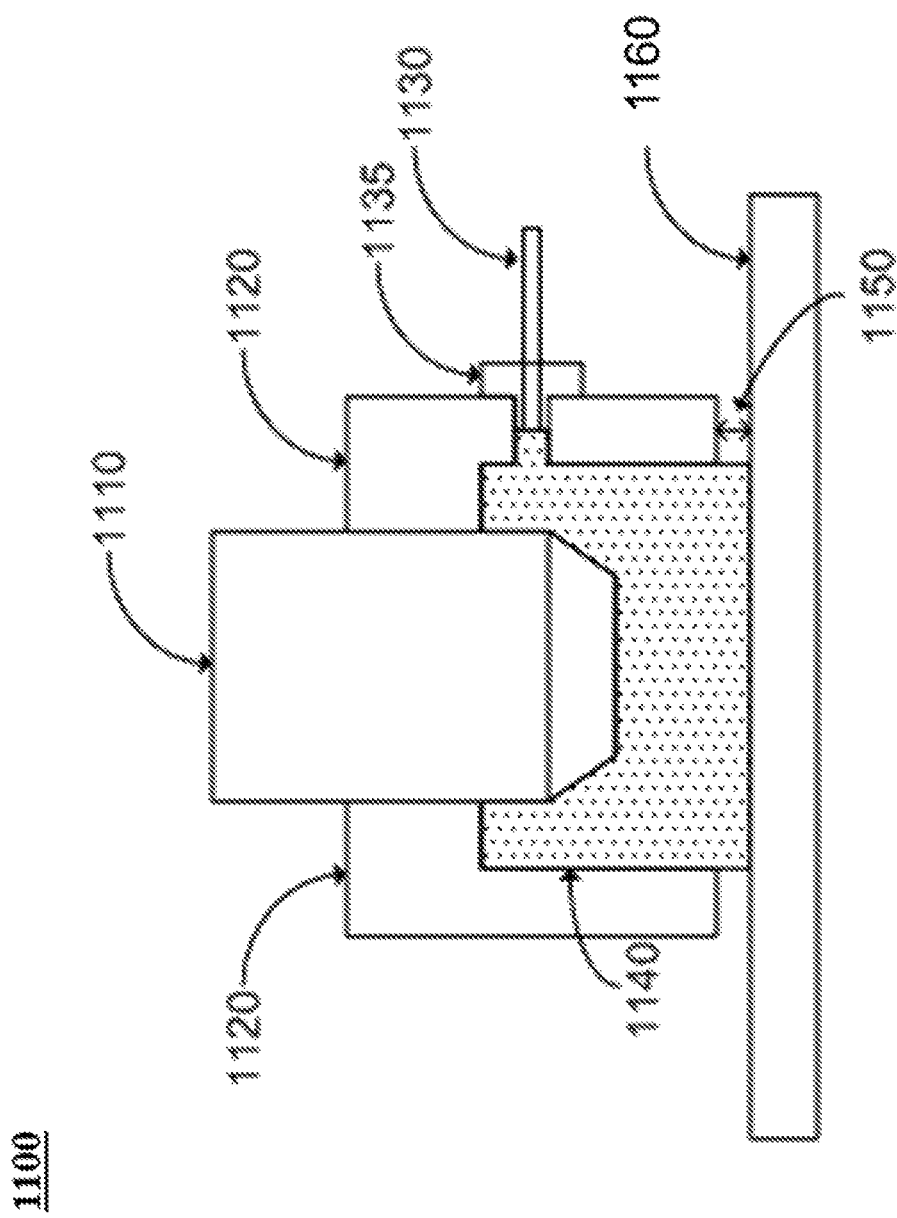

IMPLEMENTING BARRIERS FOR CONTROLLED ENVIRONMENTS DURING SAMPLE PROCESSING AND DETECTION

CROSS-REFERENCE

This application claims the benefit of U.S. Provisional Patent Application No. 62/776,866, filed Dec. 7, 2018, which application is entirely incorporated herein by reference.

BACKGROUND

Biological sample processing has various applications in the fields of molecular biology and medicine (e.g., diagnosis). For example, nucleic acid sequencing may provide information that may be used to diagnose a certain condition in a subject and in some cases tailor a treatment plan. Sequencing is widely used for molecular biology applications, including vector designs, gene therapy, vaccine design, industrial strain design and verification. Biological sample processing may involve a fluidics system and/or a detection system.

SUMMARY

Samples, including biologic samples and non-biologic samples, may be processed in a controlled environment, such as with a controlled temperature, pressure, and/or humidity. Analysis of such samples may involve detecting the samples within the controlled environment. Detection may involve continuous detection (e.g., continuous scanning), where there is continuous relative motion between a detector (e.g., optical head) and a sample. Detection may require proximity between an objective lens and the sample, such as to achieve direct or indirect contact between the objective lens and the sample. However, detection activities, such as the act of continuously scanning a sample, may disrupt the controlled environment. In some instances, efforts to maintain the controlled environment may disrupt the continuous motion of one or more detectors. In some instances, it may not be possible to move a detector within the controlled environment while maintaining the controlled environment because, for example, the presence or motion of the detector may make it difficult or impossible to seal or maintain the controlled environment, or the presence or motion of the detector may affect the sample, thus impacting the detection results. In some instances, implementing a mechanical seal, such as bellows or sliding gaskets, to maintain the controlled environment from the normal environment (e.g., room environment), may introduce unwanted forces during the detection and impede or disrupt the relative motion between the detector and the sample. Such problems may yield inaccurate and imprecise detection results. Therefore, recognized herein is a need for systems, devices, and methods that address at least the abovementioned problems.

Provided herein are barriers that can be implemented between a controlled sample environment and the external environment. Such barriers may allow for low friction or zero friction relative motion between the detector and the sample while maintaining a controlled sample environment. The barriers may allow for an objective lens to directly or indirectly (e.g., via immersion in a fluid) contact the sample during detection and movement. The barriers may allow for continuous scanning involving relative motion in a non-linear direction (e.g., in an R, θ coordinate system) and/or linear direction (e.g., in an X, Y, and/or Z coordinate system). Beneficially, such barriers may allow for continuous scanning in a 100% or substantially 100% relative humidity environment. The barriers may prevent humidity from escaping the sample environment, which when escaped can condense and affect (e.g., corrode, foul, etc.) sensitive equipment, such as the optics and electronics. Furthermore, the barriers may prevent contaminants from the external environment from entering the sample environment, which may contaminate the sample and/or affect the fluidics and/or detection (e.g., imaging).

A barrier may comprise a transition region between the sample environment and the external environment. The barrier may comprise a fluid barrier. The barrier may comprise fluids from the sample environment, the external environment, or both. The barrier may be a low pressure region. The low pressure region may have lower pressure than the sample environment, the external environment, or both. The barrier may comprise a partial vacuum. The barrier may further comprise a physical barrier.

In an aspect, provided is a method for processing a biological analyte, comprising: (a) providing a barrier between a first region and a second region, wherein the first region comprises a substrate having the biological analyte immobilized adjacent thereto, wherein the barrier maintains the first region at a first atmosphere that is different than a second atmosphere of the second region; and using a detector at least partially contained in the first region to detect one or more signals or changes thereof from the biological analyte while (i) the detector is undergoing translational motion relative to the substrate, wherein the substrate and the detector are not in direct mechanical contact, and (ii) the first region is maintained at the first atmosphere that is different than the second atmosphere of the second region.

In some embodiments, a portion of the barrier comprises fluid in bulk motion. In some embodiments, the portion of the barrier comprises a partial vacuum. In some embodiments, the portion of the barrier comprises fluid from the first region, the second region, or both.

In some embodiments, the first atmosphere is maintained at a first humidity that is different than a second humidity of the second atmosphere. In some embodiments, the first atmosphere has a relative humidity greater than 90%.

In some embodiments, the detector is an optical detector, and wherein the one or more signals are one or more optical signals or signal changes.

In some embodiments, the barrier comprises a first solid component and a second solid component, wherein the first solid component and the second solid component are not in direct mechanical contact, and wherein the first solid component is movable relative to the second solid component.

In some embodiments, a portion of the barrier comprises fluid in bulk motion, and wherein the portion is disposed between the first solid component and the second solid component.

In some embodiments, the detector is fixed relative to the first solid component and wherein the substrate is translationally fixed relative to the second solid component.

In some embodiments, the substrate is rotatable relative to the second solid component.

In some embodiments, a first part of the first solid component is provided between the first region and the second region, and wherein a second part of the first solid component is provided between the second region and a third region to form part of another barrier configured to maintain the third region at a third atmosphere that is independent of the first atmosphere and the second atmosphere, wherein a portion of the another barrier comprises fluid in bulk motion, and wherein the third region is movable relative to the first solid component independent of the first region.

In some embodiments, the second atmosphere is a room atmosphere or an ambient atmosphere.

In some embodiments, a first part of the detector is in the first region and a second part of the detector is in the second region. In some embodiments, the first part of the detector comprises an optical imaging objective at least partially immersed in an immersion fluid in contact with the substrate in the first region.

In some embodiments, the biological analyte is a nucleic acid molecule, and further comprising, based at least in part on the one or more signals or changes thereof, identifying a sequence of the nucleic acid molecule or derivative thereof.

In another aspect, provided is a method for processing a biological analyte, comprising: (a) providing a barrier between a first region and a second region, wherein the first region comprises the biological analyte, wherein the barrier maintains the first region at a first atmosphere that is different than a second atmosphere of the second region, wherein a portion of the barrier comprises fluid in bulk motion; and (b) using a detector at least partially contained in the first region to detect one or more signals or change thereof from the biological analyte while the first region is maintained at the first atmosphere that is different than the second atmosphere of the second region.

In some embodiments, the portion of the barrier comprises fluid from the first region, the second region, or both.

In some embodiments, the first atmosphere is maintained at a first humidity that is different than a second humidity of the second atmosphere. In some embodiments, the first atmosphere has a relative humidity greater than 90%.

In some embodiments, (b) comprises moving the detector relative to the biological analyte while detecting.

In some embodiments, the detector is an optical detector, and wherein the one or more signals or change thereof are one or more optical signals or change thereof.

In some embodiments, the barrier comprises a first solid component and a second solid component, wherein the first solid component and the second solid component are not in mechanical contact, and wherein the first solid component is movable relative to the second solid component.

In some embodiments, the portion of the barrier comprising the fluid is disposed between the first solid component and the second solid component.

In some embodiments, the detector is fixed relative to the first solid component and wherein the biological analyte is translationally fixed relative to the second solid component.

In some embodiments, a first part of the first solid component is provided between the first region and the second region, and wherein a second part of the first solid component is provided between the second region and a third region to form part of another barrier configured to maintain the third region at a third atmosphere that is independent of the first atmosphere and the second atmosphere, wherein a portion of the another barrier comprises fluid, and wherein the third region is movable relative to the first solid component independent of the first region.

In some embodiments, the second atmosphere is a room atmosphere or an ambient atmosphere.

In some embodiments, a first part of the detector is in the first region and a second part of the detector is in the second region. In some embodiments, the first part of the detector comprises an optical imaging objective at least partially immersed in an immersion fluid in contact with the biological analyte in the first region.

In some embodiments, the biological analyte is a nucleic acid molecule, and further comprising, based at least in part on the one or more signals or signal changes, identifying a sequence of the nucleic acid molecule or derivative thereof.

In another aspect, provided is a method for processing a biological sample, comprising: providing a barrier between a first region and a second region, wherein the first region comprises the biological sample, wherein the barrier maintains the first region at a first atmosphere that is different than a second atmosphere of the second region, wherein a portion of the barrier comprises fluid in coherent motion; and using a detector at least partially contained in the first region to detect one or more signals from the biological sample while the first region is maintained at the first atmosphere that is different than the second atmosphere of the second region.

In some embodiments, the portion of the barrier comprises fluid from the first region, the second region, or both.

In some embodiments, the portion of the barrier has a first pressure that is lower than a second pressure of the first region or a third pressure of the second region or both. In some embodiments, the portion comprises a partial vacuum.

In some embodiments, the first atmosphere is maintained at a first humidity that is different than a second humidity of the second atmosphere. In some embodiments, the first humidity is higher than the second humidity. In some embodiments, there is at least a 30% difference between the first humidity and the second humidity.

In some embodiments, the first atmosphere has a relative humidity greater than 90%.

In some embodiments, using said detector comprises moving the detector relative to the biological sample while detecting.

In some embodiments, the detector is an optical detector, and wherein the one or more signals are one or more optical signals.

In some embodiments, the first region comprises a substrate, and wherein the biological sample is immobilized to the substrate. In some embodiments, the substrate is rotatable.

In some embodiments, the barrier comprises a first solid component and a second solid component, wherein the first solid component and the second solid component are not in mechanical contact, and wherein the first solid component is movable relative to the second solid component. In some embodiments, the portion of the barrier comprising the fluid is disposed between the first solid component and the second solid component. In some embodiments, the detector is fixed relative to the first solid component and wherein the biological sample is translationally fixed relative to the second solid component.

In some embodiments, a first part of the first solid component is provided between the first region and the second region, and wherein a second part of the first solid component is provided between the second region and a third region to form part of another barrier configured to maintain the third region at a third atmosphere that is independent of the first atmosphere and the second atmosphere, wherein a portion of the another barrier comprises fluid, and wherein the third region is movable relative to the first solid component independent of the first region.

In some embodiments, the second atmosphere is a room atmosphere or an ambient atmosphere.

In some embodiments, a first part of the detector is in the first region and a second part of the detector is in the second region. In some embodiments, the first part of the detector comprises an optical imaging objective partially immersed in an immersion fluid in contact with the biological sample in the first region.

In some embodiments, the biological sample is a nucleic acid molecule, and further comprising, based at least in part on the one or more signals, identifying a sequence of the nucleic acid molecule or derivative thereof.

In another aspect, provided is a method for processing a biological sample, comprising: providing a barrier between a first region and a second region, wherein the first region comprises a substrate having the biological sample immobilized thereto, wherein the barrier maintains the first region at a first atmosphere that is different than a second atmosphere of the second region; and using a detector at least partially contained in the first region to detect one or more signals from the biological sample while (i) the detector is undergoing translational motion relative to the substrate, wherein the substrate and the detector are not in solid mechanical contact, and (ii) the first region is maintained at the first atmosphere that is different than the second atmosphere of the second region.

In some embodiments, a portion of the barrier comprises fluid in coherent motion. In some embodiments, the fluid is from the first region, the second region, or both. In some embodiments, the portion of the barrier has a first pressure that is lower than a second pressure of the first region or a third pressure of the second region or both. In some embodiments, the portion comprises a partial vacuum.

In some embodiments, the first atmosphere is maintained at a first humidity that is different than a second humidity of the second atmosphere. In some embodiments, the first humidity is higher than the second humidity. In some embodiments, there is at least a 30% difference between the first humidity and the second humidity.

In some embodiments, the first atmosphere has a relative humidity greater than 90%.

In some embodiments, the detector is an optical detector, and wherein the one or more signals are one or more optical signals.

In some embodiments, the barrier comprises a first solid component and a second solid component, wherein the first solid component and the second solid component are not in mechanical contact, and wherein the first solid component is movable relative to the second solid component.

In some embodiments, a portion of the barrier comprises fluid in coherent motion, and wherein the portion is disposed between the first solid component and the second solid component. In some embodiments, the detector is fixed relative to the first solid component and wherein the substrate is translationally fixed relative to the second solid component. In some embodiments, the substrate is rotatable relative to the second solid component.

In some embodiments, a first part of the first solid component is provided between the first region and the second region, and wherein a second part of the first solid component is provided between the second region and a third region to form part of another barrier configured to maintain the third region at a third atmosphere that is independent of the first atmosphere and the second atmosphere, wherein a portion of the another barrier comprises fluid in coherent motion, and wherein the third region is movable relative to the first solid component independent of the first region.

In some embodiments, the second atmosphere is a room atmosphere or an ambient atmosphere.

In some embodiments, a first part of the detector is in the first region and a second part of the detector is in the second region. In some embodiments, the first part of the detector comprises an optical imaging objective partially immersed in an immersion fluid in contact with the substrate in the first region.

In some embodiments, the biological sample is a nucleic acid molecule, and further comprising, based at least in part on the one or more signals, identifying a sequence of the nucleic acid molecule or derivative thereof.

In another aspect, provided is a system for processing a biological sample, comprising: a barrier disposed between a first region and a second region, wherein the first region is configured to contain the biological sample, wherein the barrier is configured to maintain the first region at a first atmosphere that is different than a second atmosphere of the second region, wherein a portion of the barrier comprises a fluid in coherent motion; and a detector at least partially contained in the first region, wherein the detector is configured to detect one or more signals from the biological sample while the first region is maintained at the first atmosphere that is different than the second atmosphere of the second region.

In some embodiments, the portion of the barrier comprises fluid from the first region, the second region, or both.

In some embodiments, the portion of the barrier has a first pressure that is lower than a second pressure of the first region or a third pressure of the second region or both. In some embodiments, the portion comprises a partial vacuum.

In some embodiments, the detector is an optical detector, and wherein the one or more signals are one or more optical signals.

In some embodiments, the first region comprises a substrate, and wherein, during use, the biological sample is immobilized to the substrate.

In some embodiments, the barrier comprises a first solid component and a second solid component, wherein the first solid component and the second solid component are not in mechanical contact, and wherein the first solid component is movable relative to the second solid component. In some embodiments, the portion of the barrier comprising the fluid in coherent motion is disposed between the first solid component and the second solid component. In some embodiments, the detector is fixed relative to the first solid component and wherein, during use, the biological sample is translationally fixed relative to the second solid component.

In some embodiments, a first part of the first solid component is provided between the first region and the second region, and wherein a second part of the first solid component is provided between the second region and a third region to form part of another barrier configured to maintain the third region at a third atmosphere that is independent of the first atmosphere and the second atmosphere, wherein a portion of the another barrier comprises fluid, and wherein the third region is movable relative to the first solid component independent of the first region.

In some embodiments, the system further comprises a fluid flow unit in fluid communication with the portion of the barrier, wherein the fluid flow unit is configured to alter or maintain a pressure of the portion of the barrier. In some embodiments, the system further comprises at least one controller operatively coupled to the detector and the fluid flow unit, wherein the at least one controller is configured to (i) direct the fluid flow unit to alter or maintain the pressure of the portion of the barrier such that the pressure is lower than a first pressure of the first region, a second pressure of the second region, or both, and (ii) direct the detector to detect the one or more signals. In some embodiments, the fluid flow unit comprises one or more fluid channels through a solid portion of the barrier.

In some embodiments, the system further comprises at least one controller operatively coupled to the detector, wherein the at least one controller is configured to direct the detector to detect the one or more signals.

In some embodiments, a first part of the detector is in the first region and a second part of the detector is in the second region. In some embodiments, the first part of the detector comprises an optical imaging objective partially immersed in an immersion fluid configured to contact the biological sample in the first region, during use.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein) of which:

FIG. 1A illustrate a cross-sectional side view of an example barrier system.

FIG. 1B illustrates a perspective view of FIG. 1A.

FIG. 1C illustrates a cross-sectional view of an example immersion optical system.

DETAILED DESCRIPTION

Figure 2A:
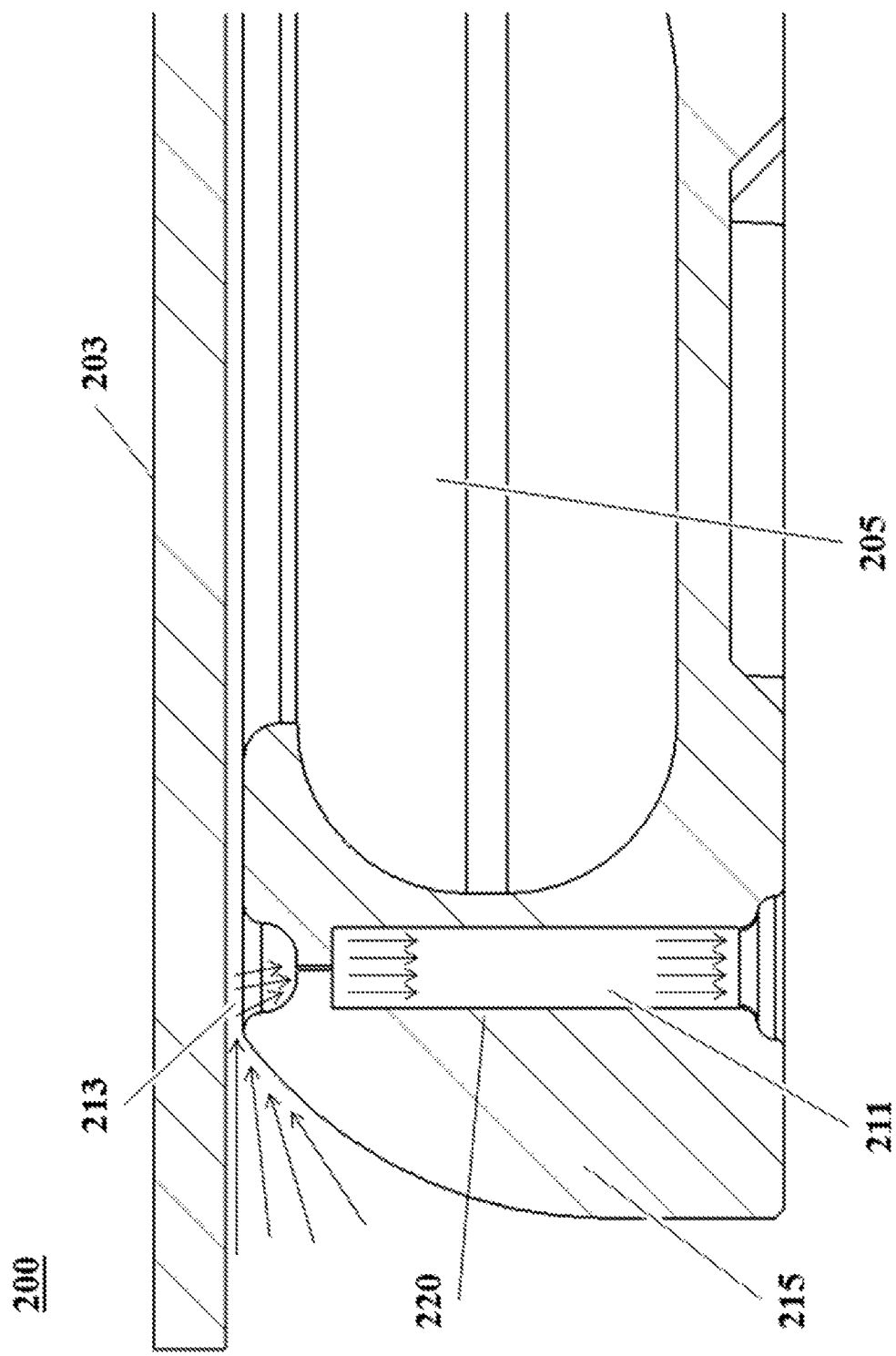
FIG. 2A illustrates a partial cross-sectional view of a barrier system maintaining a fluid barrier.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Provided herein are barriers that can be implemented between a controlled sample environment and an external environment. A barrier may comprise a transition region between the sample environment and the external environment. The barrier may comprise a fluid barrier. The barrier may comprise fluids from the sample environment, the external environment, or both. The barrier may be a low pressure region. The low pressure region may have lower pressure than the sample environment, the external environment, or both. The barrier may comprise a partial vacuum. The barrier may further comprise a physical barrier.

Beneficially, such barriers may allow for zero friction, or low friction, relative motion between the detector and the sample while maintaining the controlled sample environment. The barriers may allow for continuous scanning involving relative motion in a non-linear direction (e.g., in an R, θ coordinate system) and/or linear direction (e.g., in an X, Y, and/or Z coordinate system). The barriers may allow for continuous scanning in a 100% or substantially 100% relative humidity environment. The barriers may prevent humidity from escaping the sample environment, which when escaped can condense and affect (e.g., corrode, foul, etc.) sensitive equipment, such as the optics. Furthermore, the barriers may prevent contaminants from the external environment from entering the sample environment, which may affect the fluidics and/or detection (e.g., imaging).

The term "sample," as used herein, generally refers to a biological sample. The systems, devices, and methods provided herein may be particularly beneficial for analyzing biological samples, which can be highly sensitive to the environment, such as to the temperature, pressure, and/or humidity of the environment. Biological samples may be derived from any subject or living organism. For example, a subject may be an animal, a mammal, an avian, a vertebrate, a rodent (e.g., a mouse), a primate, a simian, a human, or other organism, such as a plant. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses).

A biological sample may comprise any number of macromolecules, for example, cellular macromolecules. The biological sample may be a cell sample. The biological sample may be a cell line or cell culture sample. The biological sample can include one or more cells. The biological sample can include one or more microbes. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

A biological sample may comprise one or more biological particles. The biological particle may be a macromolecule. The biological particle may be a small molecule. The biological particle may be a virus. The biological particle may be a cell or derivative of a cell. The biological particle may be an organelle. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be a constituent (e.g., macromolecular constituent) of a cell, such as deoxyribonucleic acids (DNA), ribonucleic acids (RNA), nucleus, organelles, proteins, peptides, polypeptides, or any combination thereof. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The biological particle may be a hardened cell. Such hardened cell may or may not include a cell wall or cell membrane. Alternatively or in addition, samples of the present disclosure may include non-biological samples.

Fluid Barriers

Provided herein are methods for processing and/or detecting a sample. In some instances, the methods can comprise providing a barrier between a first region (e.g., sample containing region) and a second region (e.g., external region), wherein the barrier maintains the first region at a first atmosphere that is different than a second atmosphere of the second region, and wherein a portion of the barrier comprises fluid in coherent motion or bulk motion. The first region can comprise the sample. Then a detector at least partially contained in the first region can detect one or more signals from the sample while the first region is maintained at the first atmosphere that is different than the second atmosphere of the second region. The detector may not be in direct mechanical contact with a substrate contained in the first region, wherein the substrate comprises the sample thereon. The detector may be in fluidic contact with the substrate.

In some instances, the methods can comprise providing a barrier between a first region (e.g., sample containing region) and a second region (e.g., external region), wherein the barrier maintains the first region at a first atmosphere that is different than a second atmosphere of the second region. The first region can comprise the sample. Then a detector at least partially contained in the first region can detect one or more signals from the sample while (i) the detector is undergoing continuous low friction or zero friction motion relative to the first region, and (ii) the first region is maintained at the first atmosphere that is different than the second atmosphere of the second region. The detector may not be in direct mechanical contact with a substrate contained in the first region, wherein the substrate comprises the sample thereon. The detector may be in fluidic contact with the substrate.

Provided herein are systems for processing and/or detecting a sample. In some instances, the systems can comprise a barrier disposed between a first region (e.g., sample-containing region) and a second region (e.g., external region), wherein the first region is configured to contain the sample, wherein the barrier is configured to maintain the first region at a first atmosphere that is different than a second atmosphere of the second region, and wherein a portion of the barrier comprises a fluid in coherent motion or bulk motion. The system can comprise a detector at least partially contained in the first region, wherein the detector is configured to detect one or more signals from the sample while the first region is maintained at the first atmosphere that is different than the second atmosphere of the second region. In some instances, the detector can be configured to detect one or more signals from the sample while the detector is undergoing continuous low friction or zero friction motion relative to the first region. In some instances, the first region may comprise a substrate comprising the sample thereon. For example, the sample may be immobilized adjacent to the substrate. In some instances, the detector may not be in direct mechanical contact with the substrate. In some instances, the detector may be in fluidic contact with the substrate.

FIGS. 1A and 1B illustrate an example barrier system 100, showing a cross-sectional side view and a perspective view, respectively. A fluid barrier 113 may be implemented between a sample environment 105 (e.g., first region) and an external environment 107 (e.g., second region). The sample environment 105 may be a controlled environment, comprising one or more samples therein. The external environment 107 may be a closed or open environment. In some instances, the external environment 107 may be a room environment or ambient environment. In some instances, the external environment 107 may also be a controlled environment.

The sample environment 105 region may be defined by a chamber 115, a plate 103, and the fluid barrier 113, wherein the fluid barrier 113 is maintained between a physical gap between the chamber 115 and the plate 103. In some instances, the physical gap may be large enough to allow fluid communication between the sample environment 105 and the external environment 107 when the fluid barrier 113 is otherwise not in place. The chamber 115 and the plate 103 may be independent such that the chamber 115, and the sample environment 105 region defined thereby, is movable relative to the plate 103. For example, the sample environment 105 region may be defined by different parts of the plate 103 with different locations of the chamber 115 relative to the plate 103. The relative motion between the chamber 115 and the plate 103 can be in any direction, such as in a non-linear direction (e.g., in an R, θ coordinate system) and/or linear direction (e.g., in an X, Y, and/or Z coordinate system). For example, the relative motion may be rotational about a central axis, or linear along any linear axis. In some instances, actuator units (e.g., linear stages, motors, etc.) and/or structural units (e.g., beams, supports, tracks, etc.) may constrain the relative motion between the chamber 115 and the plate 103.

The plate 103 and the chamber 115 may not be in direct mechanical contact, such that there is a minimal distance between the plate and the chamber. A minimal distance between the plate 103 and the chamber 115 may be at least about 100 micrometers (μm), 150 μm, 200 μm, 250 μm, 300

μm, 350 μm, 400 μm, 450 μm, 500 μm, 550 μm, 600 μm, 650 μm, 700 μm, 750 μm, 800 μm, 850 μm, 900 μm, 950 μm, 1 millimeter (mm), 2 mm, 3 mm, 4 mm, 5 mm, 6 mm, 7 mm, 8 mm, 9 mm, 1 centimeter (cm), or more. Alternatively or in addition, the minimal distance may be at most about 1 cm, 9 mm, 8 mm, 7 mm, 6 mm, 5 mm, 4 mm, 3 mm, 2 mm, 1 mm, 950 μm, 900 μm, 850 μm, 800 μm, 750 μm, 700 μm, 650 μm, 600 μm, 550 μm, 500 μm, 450 μm, 400 μm, 350 μm, 300 μm, 250 μm, 200 μm, 150 μm, 100 μm, or less. Alternatively or in addition, the minimal distance may be within a range defined by any two of the preceding values.

The fluid barrier 113 may act as a transition region between the sample environment 105 and the external environment 107. The fluid barrier 113 may comprise fluids (e.g., air) from the sample environment, the external environment, or both. The fluid barrier 113 may be a low pressure region. The fluid barrier 113 may have lower pressure than the sample environment, the external environment, or both. The barrier may comprise a partial vacuum. In some instances, the fluid barrier 113 may be a high pressure region. For example, the fluid barrier may have a higher pressure than the sample environment, the external environment, or both. The fluid barrier 113 may be in coherent motion, such as in a coherent direction of flow. The fluid barrier 113 may be in bulk motion. The fluid barrier may comprise volumes of fluid that has a net average motion oriented along one or more directions, or towards a reference destination. In some instances, a volume of fluid in coherent motion or bulk motion may have stream lines that are oriented along the same general direction. Fluid in coherent motion or bulk motion may be differentiated from fluid in random motion that are not part of the fluid barrier (e.g., not in coherent motion, not in bulk motion, not having net average motion). Fluid in the fluid barrier may have turbulent flow and/or laminar flow.

The sample environment 105 may comprise a substrate. One or more samples may be immobilized on or adjacent to the substrate. Alternatively or in addition, the one or more samples may otherwise be disposed on the substrate. In some instances, at least a part of the chamber 115 may be or comprise a substrate. In other instances, the chamber 115 may be coupled to a substrate. In some instances, the substrate may be fixed relative to the chamber 115. Alternatively, the substrate may be movable relative to the chamber 115, for example, in a linear and/or non-linear (e.g., rotational) direction. For example, the substrate may be translationally fixed to the chamber 115, but rotatable relative to the chamber 115. Where both the chamber 115 is movable relative to the plate 103 and the substrate is movable relative to the chamber 115, the two relative motions may or may not be operated by the same actuator units.

A detector 101 may protrude into the sample environment 105 from the external environment 107 through the plate 103, such as through an aperture in the plate 103. The fit between the detector 101 and the aperture may be fluid-tight such that there is no fluid communication through the aperture when the detector 101 is fitted through the aperture. Alternatively or in addition, the aperture may be hermetically sealed. Alternatively, the plate 103 may be integral to the detector 101. Alternatively, the detector 101 may be entirely contained in the sample environment 105, for example, by affixing a non-sample facing end to the plate 103.

At least a portion of the detector 101 may be fixed relative to the plate 103. In some instances, the detector 101 may be capable of translating along an axis that is substantially normal to the plane of the plate 103 (e.g., through the aperture) independent of the plate 103. In some instances, at least a portion of the detector 101 (e.g., a portion of the detector inside the sample environment region) may be capable of moving (e.g., linearly or nonlinearly, such as rotating) independent of the plate 103.

Within the sample environment 105, the detector 101 may be configured to detect the one or more samples disposed on the substrate using an immersion optical system, wherein a portion of the detector inside the sample environment 105, such as an optical imaging objective, is in optical communication with the substrate through a liquid fluid 131 medium. In some instances, the liquid fluid medium may be disposed on a local region of the substrate. In other instances, the liquid fluid medium may be disposed across an entire area of a surface of the substrate (e.g., across a base of chamber 115). Alternatively, the detector may be in optical communication with the substrate without the liquid fluid medium.

FIG. 1C illustrates a cross-sectional view of an example immersion optical system 1100. The system 1100 may be used to optically image the substrates described herein. The system 1100 may be integrated with any barrier system described elsewhere herein. The system may comprise an optical imaging objective 1110 (e.g., detector 101). For example, the objective may have protruded into the sample environment (e.g., through plate 103) or may be contained within the sample environment (e.g., and affixed to a surface of the plate 103). The optical imaging objective may be an immersion optical imaging objective. The optical imaging objective may be configured to be in optical communication with a substrate 1160. The optical imaging objective may be partially or completely surrounded by an enclosure 1120. The enclosure may partially or completely surround a sample-facing end of the optical imaging objective. The enclosure may be fixed to the optical imaging objective and/or to the plate. The enclosure may have a generally cup-like shape or form. The enclosure may be any container. The enclosure may be configured to contain a fluid 1140 (such as water or an aqueous solution or oil or an organic solution) in which the optical imaging objective is to be immersed. The fluid may be in contact with the substrate 1160.

The enclosure 1120 may be configured to maintain a minimal distance 1150 between the substrate and the enclosure in order to avoid contact between the enclosure and the substrate 1160 during movement of the substrate relative to the plate. The minimal distance may be at least about 100 nanometers (nm), at 200 nm, 300 nm, 400 nm, 500 nm, 1 micrometer (μm), 2 μm, 3 μm, 4 μm, 5 μm, 10 μm, 20 μm, 30 μm, 40 μm, 50 μm, 100 μm, 200 μm, 300 μm, 400 μm, 500 μm, 1 millimeter (mm) or more. Alternatively or in addition, the minimal distance may be at most about 1 mm, 500 μm, 400 μm, 300 μm, 200 μm, 100 μm, 50 μm, 40 μm, 30 μm, 20 μm, 10 μm, 5 μm, 4 μm, 3 μm, 2 μm, 1 μm, 500 nm, 400 nm, 300 nm, 200 nm, 100 nm or less. Alternatively or in addition, the minimal distance may be within a range defined by any two of the preceding values. Even with a minimal distance, the enclosure may contain the fluid due to surface tension effects. The system may comprise a fluid flow tube 1130 configured to deliver fluid 1140 to the inside of the enclosure. The fluid flow tube may be connected to the enclosure through an adaptor 1135. The adaptor may comprise a threaded adaptor, a compression adaptor, or any other adaptor.

In some instances, an electrical field application unit (not shown) can be configured to regulate a hydrophobicity of one or more surfaces of a container to retain at least a portion of the fluid contacting the immersion objective lens and the open substrate, such as by applying an electrical field.

The optical imaging objective 1110 and enclosure 1120 may provide a physical barrier between a first location on the substrate in which chemical processing operations are performed and a second location on the substrate in which detection operations are performed. In this manner, the chemical processing operations and the detection operations may be performed with independent operation conditions and contamination of the detector may be avoided. The first and second locations may have different humidities, temperatures, pressures, or atmospheric admixtures.

Figure 2B:
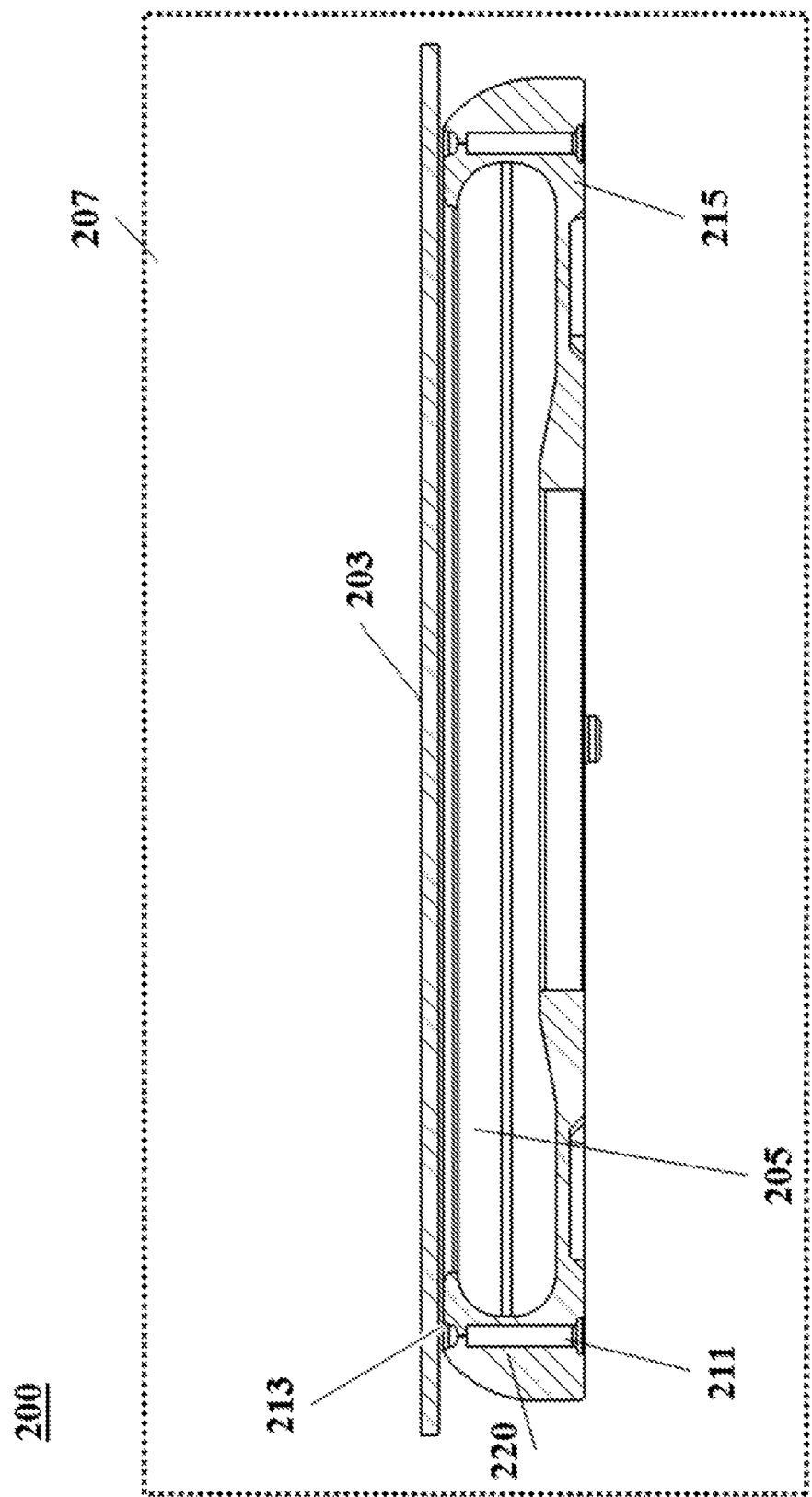
FIG. 2B illustrates a zoomed out view of the barrier system of FIG. 2A.
Figure 2C:
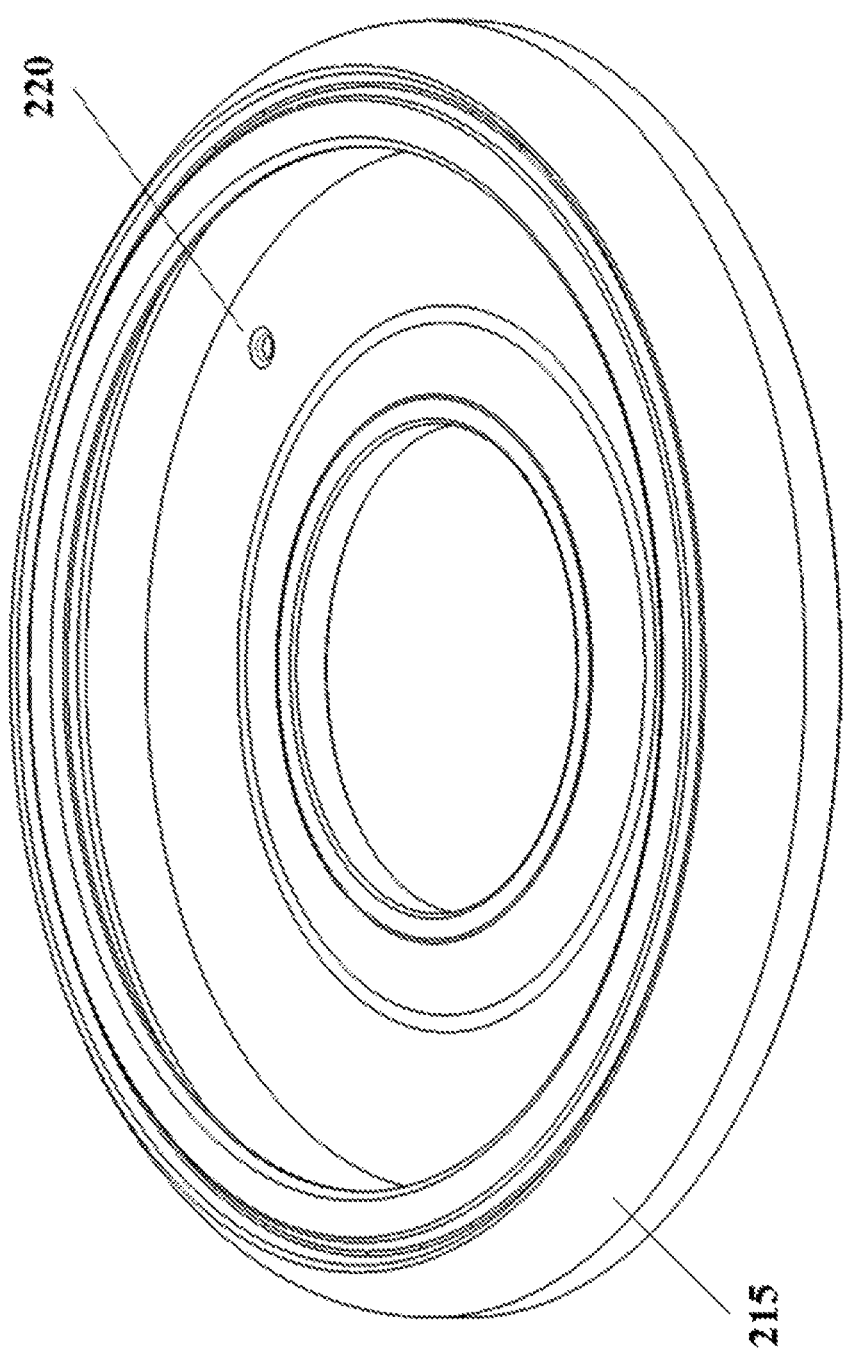
FIG. 2C illustrates a perspective view of a chamber of the barrier system of FIG. 2A.

FIG. 2A illustrates a partial cross-sectional view of a barrier system 200 maintaining a fluid barrier 213. FIG. 2B illustrates a zoomed out view of the barrier system 200. FIG. 2C illustrates a perspective view of a chamber 215 of the barrier system 200. The barrier system 200, and/or respective components thereof, may correspond to the barrier system 100, and/or respective components thereof.

The barrier system 200 comprises a sample environment 205 defined by a plate 203, the chamber 215, and the fluid barrier 213. The chamber 215 and the plate 203 may be separated by a physical gap. The sample environment 205 may be isolated (and/or insulated) from an external environment 207.

The fluid barrier 213 may act as a transition region between the sample environment 205 and the external environment 207. The fluid barrier 213 may comprise fluids (e.g., air) from the sample environment 205, the external environment 207, or both. The fluid barrier 213 may be a low pressure region. The fluid barrier 213 may have lower pressure than the sample environment, the external environment, or both. The fluid barrier 213 may be maintained via a fluid flow unit, such as a pressure-altering apparatus 211. The fluid barrier 213 may comprise fluid in coherent motion or bulk motion.

The pressure-altering apparatus 211 may be integral to the chamber 215. For example, as illustrated in FIGS. 2A-2C, the pressure-altering apparatus may be integrated as a fluid channel 220 in a wall of the chamber 215. For example, suction may be applied through the fluid channel 220 to draw in fluids from the external environment 207, or sample environment 205, or both, to generate a partial vacuum curtain (e.g., in coherent motion, in bulk motion, etc.), thereby creating the fluid barrier 213. The fluid exhaust may be expelled at another end of the fluid channel. Alternatively or in addition, the apparatus may not be integral to the chamber 215. The fluid flow unit and/or the pressure-altering apparatus 211 may be operated via one or more compressors (e.g., to generate negative pressure), pumps (e.g., to generate positive pressure), suction apparatus, and/or other devices to provide the lower pressure in the transition region. The chamber 215 may comprise one or more fluid channels 220 for implementing fluid barriers of the present disclosure.

While two pressure-altering apparatus 211 is illustrated in FIGS. 2A-2C, it will be appreciated that there may be any number of such apparatus. For example, there may be at least about 2, 3, 4, 5, 6, 7, 8, 9, 10, 20, 30, 40, 50 or more such apparatus. Alternatively or in addition, there may be at most about 50, 40, 30, 20, 10, 9, 8, 7, 6, 5, 4, 3, or 2 such apparatus. In some instances, one or more pressure-altering apparatus 211 may be implemented as an annular fluid channel surrounding the sample environment region, or other fluid channel along a perimeter or boundary of the sample environment region.

Beneficially, the fluid barrier 213 may provide a low friction or zero friction seal between the sample environment 205 and the external environment 207. In some instances, a fluid flow rate through the fluid barrier 213 may be at least about 5 liters per minute (L/min), 5.5 L/min, 6 L/min, 6.5 L/min, 7 L/min, 7.5 L/min, 8 L/min, 8.5 L/min, 9 L/min, 9.5 L/min, 10 L/min, 10.5 L/min, 11 L, 11.5 L/min, 12 L/min, 12.5 L/min, 13 L/min, 13.5 L/min, 14 L/min, 14.5 L/min, 15 L/min, or more. Alternatively or in addition, the fluid flow rate may be at most about 15 L/min, 14.5 L/min, 14 L/min, 13.5 L/min, 13 L/min, 12.5 L/min, 12 L/min, 11.5 L/min, 11 L/min, 10.5 L/min, 10 L/min, 9.5 L/min, 9 L/min, 8.5 L/min, 8 L/min, 7.5 L/min, 7 L/min, 6.5 L/min, 6 L/min, 5.5 L/min, 5 L/min, or less. As will be appreciated the fluid flow rate may vary with different parameters (e.g., minimal distance between the plate and chamber, pressure, temperature, etc.). In an example, for a gap of about 500 microns between the plate 203 and the chamber 215, the fluid flow rate can be about 10 L/min or about 13 milliliters per minute (mL/min) per millimeter (mm) along the circumference for a velocity of about 0.42 meters per second (m/s).

Figure 3:
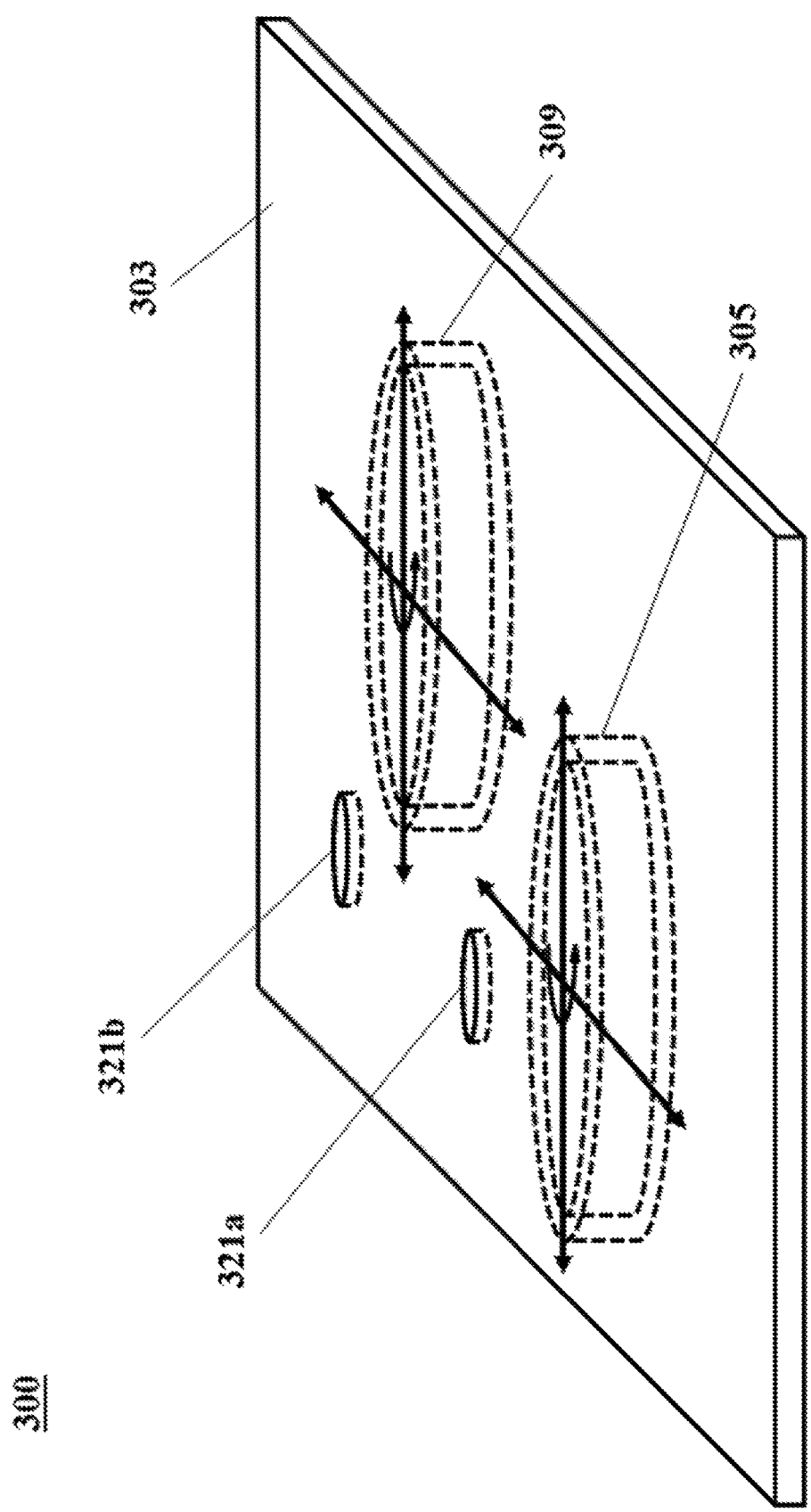
FIG. 3 illustrates a barrier system having multiple sample environments.

The systems of the present disclosure may be scaled, such as to have multiple sample environment regions defined by the same plate. FIG. 3 illustrates a barrier system 300 having multiple sample environments. The barrier system 300, and/or respective components thereof, may correspond to any other barrier system described herein (e.g., 100 and/or 200) and/or respective components thereof.

A single plate 303 may define at least two independent sample environments 305, 309, which are further defined by two independent chambers. Each sample environment may be controlled and maintained independent of other sample environments. Each sample environment may be movable relative to the plate 303 independent of the other sample environments. A fluid barrier may be maintained between each sample environment and the external environment.

While two sample environments are illustrated in FIG. 3, it will be appreciated that systems of the present disclosure may be implemented for any number of sample environments using a single plate. For example, there may be at least about 2, 3, 4, 5, 6, 7, 8, 9, 10, 20, 30, 40, 50 or more such sample environments in a single plate system. Alternatively or in addition, there may be at most about 50, 40, 30, 20, 10, 9, 8, 7, 6, 5, 4, 3, or 2 such sample environments. Any subset of, or all of, the multiple sample environments may be capable of moving independently of other sample environments.

In some instances, a single detector in the plate 303 may be used to detect one or more sample environments. Alternatively or in addition, a single plate 303 may allow at least two detectors to protrude through the single plate 303 to detect in parallel. For example, such detectors may protrude through the plate via one or more apertures 321a, 321b which have fluid-tight fits with the detectors. The detectors may be fixed relative to the plate. In some instances, the multiple detectors may detect two different locations in the same sample environment in parallel. In some instances, the multiple detectors may detect at least two different sample environments in parallel.

While two detector apertures are illustrated in FIG. 3, it will be appreciated that systems of the present disclosure may be implemented for any number of detectors using a single plate. For example, there may be at least about 2, 3, 4, 5, 6, 7, 8, 9, 10, 20, 30, 40, 50 or more detectors in a single plate system. Alternatively or in addition, there may be at most about 50, 40, 30, 20, 10, 9, 8, 7, 6, 5, 4, 3, or 2 such detectors.

The sample environments (e.g., 105, 205, 305, 309) of the present disclosure may be controlled. For instance, the environment may be maintained at a specified temperature or humidity. The environment (or any element thereof) may be maintained at a temperature of at least about 20 degrees Celsius (° C.), 25° C., 30° C., 35° C., 40° C., 45° C., 50° C., 55° C., 60° C., 65° C., 70° C., 75° C., 80° C., 85° C., 90° C., 95° C., 100° C. or higher. Alternatively, the environment may be maintained at less than 20° C. Alternatively or in addition, the environment (or any element thereof) may be maintained at a temperature of at most about 100° C., 95° C., 90° C., 85° C., 80° C., 75° C., 70° C., 65° C., 60° C., 55° C., 50° C., 45° C., 40° C., 35° C., 30° C., at 25° C., 20° C., or lower. The environment may be maintained at a temperature that is within a range defined by any two of the preceding values. Different elements of the sample environment, such as the chamber, protruding portion of the detector, immersion fluid, plate, substrates, solutions, and/or samples therein may be maintained at different temperatures or within different temperature ranges, such as the temperatures or temperature ranges described herein. Elements of the system may be set at temperatures above the dewpoint to prevent condensation. Elements of the system may be set at temperatures below the dewpoint to collect condensation.

In some instances, the sample environments may be maintained at higher humidity than an external environment. In some instances, the sample environments may be maintained at a relative humidity of at least about 5%, 10%, 15%, 20%, 25%, 30%, 35%, 40%, 45%, 50%, 55%, 60%, 65%, 70%, 75%, 80%, 85%, 90%, 95%, or 100%. Alternatively or in addition, the relative humidity may be maintained at at most about 100%, 95%, 90%, 85%, 80%, 75%, 70%, 65%, 60%, 55%, 50%, 45%, 40%, 35%, 30%, 25 20%, 15%, 10%, 5%, or less. Alternatively or in addition, the relative humidity may be maintained within a range defined by any two of the preceding values.

An environmental unit (e.g., humidifiers, heaters, heat exchangers, compressors, etc.) may be configured to regulate one or more operating conditions in each sample environment. In some instances, each environment may be regulated by independent environmental units. In some instances, a single environmental unit may regulate a plurality of environments. In some instances, a plurality of environmental units may, individually or collectively, regulate the different environments. An environmental unit may use active methods or passive methods to regulate the operating conditions. For example, the temperature may be controlled using heating or cooling elements. The humidity may be controlled using humidifiers or dehumidifiers. In some instances, a first part of the sample environment may be further controlled from other parts of the sample environment. Different parts may have different local temperatures, pressures, and/or humidity. For example, the sample environment may comprise a first internal environment and a second internal environment separated by a seal. In some instances, the seal may comprise an immersion objective lens, as described elsewhere herein. For example, the immersion objective lens may be part of a seal that separates the sample environment into a first internal environment having 100% (or substantially 100%) relative humidity and a second environment having a different temperature, pressure or humidity. The second environment may or may not be an ambient environment. The immersion objective lens may be in contact a detector.

External environments (e.g., 107, 207) of the present disclosure may be any environment external to the sample environments. For example, the external environment may be a room environment. The external environment may be an ambient environment. The external environment may itself be controlled, such as via one or more environmental units described elsewhere herein. The external environment may be open or closed. In some instances, the external environment may be at room temperature, pressure, and/or humidity. In some instances, the external environment may be at ambient temperature, pressure, and/or humidity.

Chambers (e.g., 115, 215) of the present disclosure may comprise a base and side walls to define an opening that nearly contacts the plate. The side walls may be a closed continuous surface, or a plurality of adjacent (and/or adjoining) surfaces. For example, the base may comprise or be the substrate. In some instances, the base may be coupled to the substrate. The substrate may be translationally fixed to the base, but rotatable relative to the base. In some instances, at least a portion of a side wall of the chamber may have thickness dimensions large enough to allow integration of one or more fluid channels to allow operation of the pressure-altering apparatus. In some instances, a side wall of the chamber may have thickness dimensions large enough to maintain the low pressure fluid barrier. The chamber may entirely or partially comprise one or more of glass, silicon, a metal such as aluminum, copper, titanium, chromium, or steel, a ceramic such as titanium oxide or silicon nitride, a plastic such as polyethylene (PE), low-density polyethylene (LDPE), high-density polyethylene (HDPE), polypropylene (PP), polystyrene (PS), high impact polystyrene (HIPS), polyvinyl chloride (PVC), polyvinylidene chloride (PVDC), acrylonitrile butadiene styrene (ABS), polyacetylene, polyamides, polycarbonates, polyesters, polyurethanes, polyepoxide, polymethyl methacrylate (PMMA), polytetrafluoroethylene (PTFE), phenol formaldehyde (PF), melamine formaldehyde (MF), urea-formaldehyde (UF), polyetheretherketone (PEEK), polyetherimide (PEI), polyimides, polylactic acid (PLA), furans, silicones, polysulfones, any mixture of any of the preceding materials, or any other appropriate material.

Substrates of the present disclosure may be an open substrate. The substrate may be a solid substrate. The substrate may entirely or partially comprise one or more of glass, silicon, a metal such as aluminum, copper, titanium, chromium, or steel, a ceramic such as titanium oxide or silicon nitride, a plastic such as polyethylene (PE), low-density polyethylene (LDPE), high-density polyethylene (HDPE), polypropylene (PP), polystyrene (PS), high impact polystyrene (HIPS), polyvinyl chloride (PVC), polyvinylidene chloride (PVDC), acrylonitrile butadiene styrene (ABS), polyacetylene, polyamides, polycarbonates, polyesters, polyurethanes, polyepoxide, polymethyl methacrylate (PMMA), polytetrafluoroethylene (PTFE), phenol formaldehyde (PF), melamine formaldehyde (MF), urea-formaldehyde (UF), polyetheretherketone (PEEK), polyetherimide (PEI), polyimides, polylactic acid (PLA), furans, silicones, polysulfones, any mixture of any of the preceding materials, or any other appropriate material. The substrate may be entirely or partially coated with one or more layers of a metal such as aluminum, copper, silver, or gold, an oxide such as a silicon oxide ($Si_xO_y$, where x, y may take on any possible values), a photoresist such as SU8, a surface coating such as an aminosilane or hydrogel, polyacrylic acid, polyacrylamide dextran, polyethylene glycol (PEG), or any combination of any of the preceding materials, or any other appropriate coating. The one or more layers may have a thickness of at least 1 nanometer (nm), at least 2 nm, at least 5 nm, at least 10 nm, at least 20 nm, at least 50 nm, at least 100 nm, at least 200 nm, at least 500 nm, at least 1 micrometer (μm), at least 2 μm, at least 5 μm, at least 10 μm, at least 20 μm, at least 50 μm, at least 100 μm, at least 200 μm, at least 500 μm, or at least 1 millimeter (mm). The one or more layers may have a thickness that is within a range defined by any two of the preceding values.

The substrate and/or chamber may have any shape, form or dimension. In some instances, for example, the substrate may have the general form of a cylinder, a cylindrical shell or disk, a rectangular prism, or any other geometric form. The substrate may have a thickness (e.g., a minimum dimension) of at least about 100 μm, 200 μm, 300 μm, 400 μm, 500 μm, 1 mm, 2 mm, 3 mm, 4 mm, 5 mm, 1 cm, 2 cm, 3 cm, 4 cm, 5 cm or more. The substrate may have a thickness that is within a range defined by any two of the preceding values. The substrate may have a first lateral dimension (such as a width for a substrate having the general form of a rectangular prism or a radius for a substrate having the general form of a cylinder) of at least about 1 mm, 2 mm, 3 mm, 4 mm, 5 mm, 1 cm, 2 cm, 3 cm, 4 cm, 5 cm, 6 cm, 7 cm, 8 cm, 9 cm, 10 cm, 20 cm, 30 cm, 40 cm, 50 cm, 60 cm, 70 cm, 80 cm, 90 cm, 1 meter (m) or more. The substrate may have a first lateral dimension that is within a range defined by any two of the preceding values. The substrate may have a second lateral dimension (such as a length for a substrate having the general form of a rectangular prism) or at least at least about 1 mm, 2 mm, 3 mm, 4 mm, 5 mm, 1 cm, 2 cm, 3 cm, 4 cm, 5 cm, 6 cm, 7 cm, 8 cm, 9 cm, 10 cm, 20 cm, 30 cm, 40 cm, 50 cm, 60 cm, 70 cm, 80 cm, 90 cm, 1 meter (m) or more. The substrate may have a second lateral dimension that is within a range defined by any two of the preceding values. A surface of the substrate may be planar or substantially planar. Alternatively or in addition to, a surface of the substrate may be textured or patterned. For example, the substrate may comprise grooves, troughs, hills, and/or pillars. In some instances, the substrate may comprise wells. In some instances, the substrate may define one or more cavities (e.g., micro-scale cavities or nano-scale cavities). The substrate may have a regular textures and/or patterns across the surface of the substrate. For example, the substrate may have regular geometric structures (e.g., wedges, cuboids, cylinders, spheroids, hemispheres, etc.) above or below a reference level of the surface. Alternatively, the substrate may have irregular textures and/or patterns across the surface of the substrate. For example, the substrate may have any arbitrary structure above or below a reference level of the substrate. In some instances, a texture of the substrate may comprise structures having a maximum dimension of at most about 100%, 90%, 80%, 70%, 60%, 50%, 40%, 30%, 20%, 10%, 9%, 8%, 7%, 6%, 5%, 4%, 3%, 2%, 1%, 0.1%, 0.01%, 0.001%, 0.0001%, 0.00001% of the total thickness of the substrate or a layer of the substrate. In some instances, the textures and/or patterns of the substrate may define at least part of an individually addressable location on the substrate. A textured and/or patterned substrate may be substantially planar.

Figure 4:
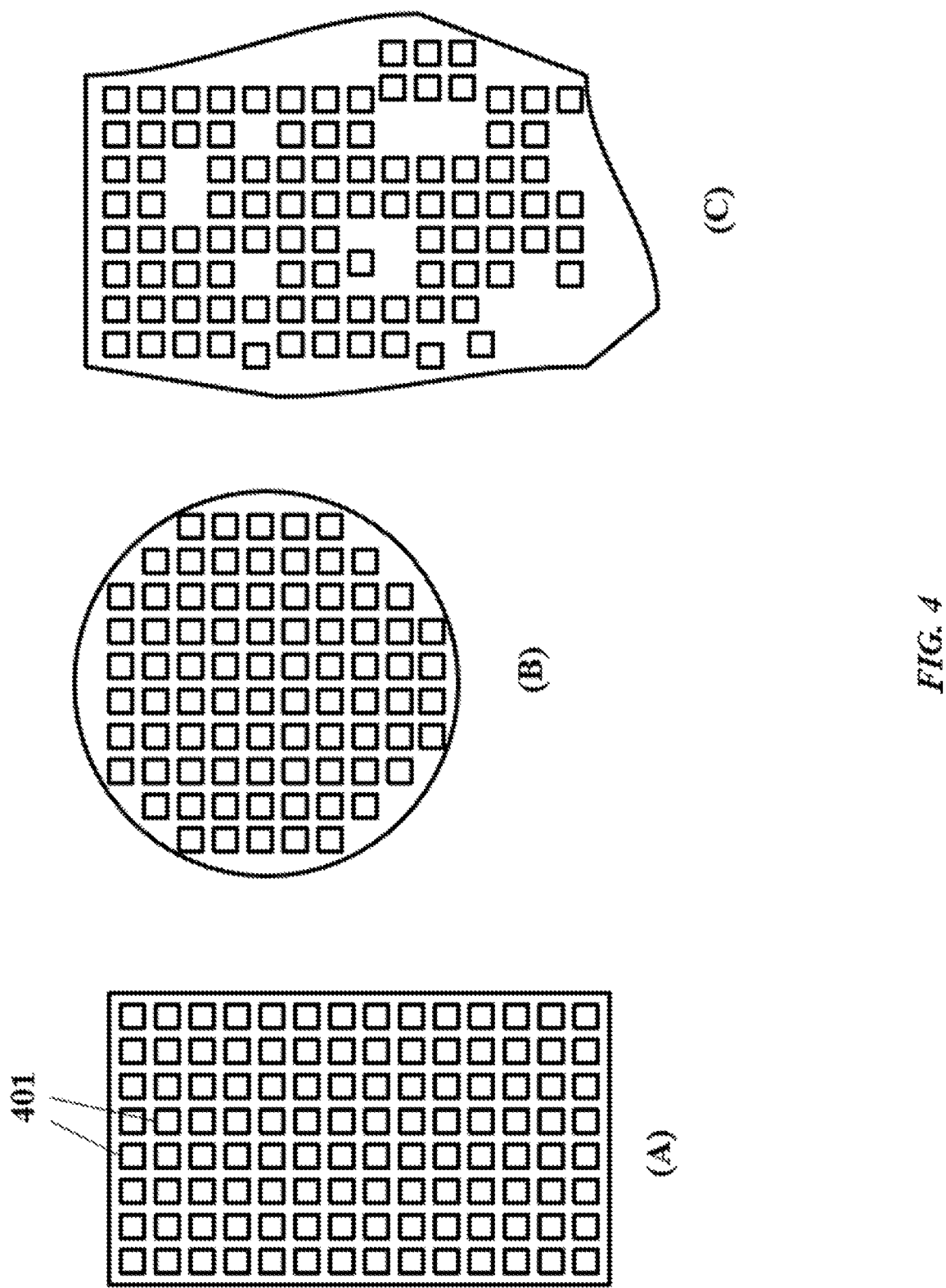
FIG. 4 illustrates examples of arrays on a substrate.

The substrate may comprise an array. For instance, the array may be located on a lateral surface of the substrate. The array may be a planar array. The array may have the general shape of a circle, annulus, rectangle, or any other shape. The array may comprise linear and/or non-linear rows. The array may be evenly spaced or distributed. The array may be arbitrarily spaced or distributed. The array may have regular spacing. The array may have irregular spacing. The array may be a textured array. The array may be a patterned array. FIG. 4 illustrates examples of arrays of individually addressable locations 401 on a substrate (e.g., from a top view), with panel A showing a substantially rectangular substrate with regular linear arrays, panel B showing a substantially circular substrate with regular linear arrays, and panel C showing an arbitrarily shaped substrate with irregular arrays.

The array may comprise a plurality of individually addressable locations (e.g., 401). In some instances, the locations may correspond to individually addressable coordinates on the substrate. Alternatively or in addition, the locations may correspond to physical structures (e.g., wells) on the substrate. An analyte to be processed and/or detected by the detector may be immobilized to the array. The array may comprise one or more binders described herein, such as one or more physical linkers or adapters or chemical linkers or adapters that are coupled to, or configured to couple to, an analyte. For instance, the array may comprise a linker or adaptor that is coupled to a nucleic acid molecule. Alternatively or in addition to, the analyte may be coupled to a bead, and the bead may be immobilized to the array.

The individually addressable locations may comprise locations of analytes or groups of analytes that are accessible for manipulation. The manipulation may comprise placement, extraction, reagent dispensing, seeding, heating, cooling, or agitation. The extraction may comprise extracting individual analytes or groups of analytes. For instance, the extraction may comprise extracting at least 2, at least 5, at least 10, at least 20, at least 50, at least 100, at least 200, at least 500, or at least 1,000 analytes or groups of analytes. Alternatively or in addition to, the extraction may comprise extracting at most 1,000, at most 500, at most 200, at most 100, at most 50, at most 20, at most 10, at most 5, or at most 2 analytes or groups of analytes. The manipulation may be accomplished through, for example, localized microfluidic, pipet, optical, laser, acoustic, magnetic, and/or electromagnetic interactions with the analyte or its surroundings.

The array may be coated with binders. For instance, the array may be randomly coated with binders. Alternatively, the array may be coated with binders arranged in a regular pattern (e.g., in linear arrays, radial arrays, hexagonal arrays etc.). The array may be coated with binders on at least 10%, at least 20%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, or at least 99% of the number of individually addressable locations, or of the surface area of the substrate. The array may be coated with binders on a fraction of individually addressable locations, or of the surface areas of the substrate, that is within a range defined by any two of the preceding values. The binders may be integral to the array. The binders may be added to the array. For instance, the binders may be added to the array as one or more coating layers on the array.

The binders may immobilize analytes through non-specific interactions, such as one or more of hydrophilic interactions, hydrophobic interactions, electrostatic interactions, physical interactions (for instance, adhesion to pillars or settling within wells), and the like. In some instances, the binders may immobilize biological analytes through specific interactions. For instance, where a biological analyte is a nucleic acid molecule, the binders may comprise oligonucleotide adaptors configured to bind to the nucleic acid molecule. Alternatively or in addition, such as to bind other types of analytes, the binders may comprise one or more of antibodies, oligonucleotides, aptamers, affinity binding proteins, lipids, carbohydrates, and the like. The binders may immobilize biological analytes through any possible combination of interactions. For instance, the binders may immobilize nucleic acid molecules through a combination of physical and chemical interactions, through a combination of protein and nucleic acid interactions, etc. The array may comprise at least about 10, 100, 1000, 10,000, 100,000, 1,000,000, 10,000,000, 100,000,000 or more binders. Alternatively or in addition, the array may comprise at most about 100,000,000, 10,000,000, 1,000,000, 100,000, 10,000, 1000, 100, 10 or fewer binders. The array may have a number of binders that is within a range defined by any two of the preceding values. In some instances, a single binder may bind a single analyte (e.g., nucleic acid molecule). In some instances, a single binder may bind a plurality of analytes (e.g., plurality of nucleic acid molecules). In some instances, a plurality of binders may bind a single analyte. Though some examples herein describe interactions of binders with nucleic acid molecules, the binders may immobilize other molecules (such as proteins), other particles, cells, viruses, other organisms, or the like, and non-biological analytes.

In some instances, each location, or a subset of such locations, may have immobilized thereto an analyte (e.g., a nucleic acid molecule, a protein molecule, a carbohydrate molecule, etc.). In other instances, a fraction of the plurality of individually addressable location may have immobilized thereto an analyte. A plurality of analytes immobilized to the substrate may be copies of a template analyte. For example, the plurality of analytes (e.g., nucleic acid molecules) may have sequence homology. In other instances, the plurality of analytes immobilized to the substrate may not be copies. The plurality of analytes may be of the same type of analyte (e.g., a nucleic acid molecule) or may be a combination of different types of analytes (e.g., nucleic acid molecules, protein molecules, etc.).

In some instances, the array may comprise a plurality of types of binders, such as to bind different types of analytes. For example, the array may comprise a first type of binders (e.g., oligonucleotides) configured to bind a first type of analyte (e.g., nucleic acid molecules), and a second type of binders (e.g., antibodies) configured to bind a second type of analyte (e.g., proteins), and the like. In another example, the array may comprise a first type of binders (e.g., first type of oligonucleotide molecules) to bind a first type of nucleic acid molecules and a second type of binders (e.g., second type of oligonucleotide molecules) to bind a second type of nucleic acid molecules, and the like. For example, the substrate may be configured to bind different types of analytes in certain fractions or specific locations on the substrate by having the different types of binders in the certain fractions or specific locations on the substrate.

An analyte may be immobilized to the array at a given individually addressable location of the plurality of individually addressable locations. An array may have any number of individually addressable locations. For instance, the array may have at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, at least 1,000,000, at least 2,000,000, at least 5,000,000, at least 10,000,000, at least 20,000,000, at least 50,000,000, at least 100,000,000, at least 200,000,000, at least 500,000,000, at least 1,000,000,000, at least 2,000,000,000, at least 5,000,000,000, at least 10,000,000,000, at least 20,000,000,000, at least 50,000,000,000, or at least 100,000,000,000 individually addressable locations. The array may have a number of individually addressable locations that is within a range defined by any two of the preceding values. Each individually addressable location may be digitally and/or physically accessible individually (from the plurality of individually addressable locations). For example, each individually addressable location may be located, identified, and/or accessed electronically or digitally for mapping, sensing, associating with a device (e.g., detector, processor, dispenser, etc.), or otherwise processing. Alternatively or in addition to, each individually addressable location may be located, identified, and/or accessed physically, such as for physical manipulation or extraction of an analyte, reagent, particle, or other component located at an individually addressable location.

Each individually addressable location may have the general shape or form of a circle, rectangle, pit, bump, or any other shape or form. Each individually addressable location may have a first lateral dimension (such as a radius for individually addressable locations having the general shape of a circle or a width for individually addressable locations having the general shape of a rectangle). The first lateral dimension may be at least 1 nanometer (nm), at least 2 nm, at least 5 nm, at least 10 nm, at least 20 nm, at least 50 nm, at least 100 nm, at least 200 nm, at least 500 nm, at least 1,000 nm, at least 2,000 nm, at least 5,000 nm, or at least 10,000 nm. The first lateral dimension may be within a range defined by any two of the preceding values. Each individually addressable location may have a second lateral dimension (such as a length for individually addressable locations having the general shape of a rectangle). The second lateral dimension may be at least 1 nanometer (nm), at least 2 nm, at least 5 nm, at least 10 nm, at least 20 nm, at least 50 nm, at least 100 nm, at least 200 nm, at least 500 nm, at least 1,000 nm, at least 2,000 nm, at least 5,000 nm, or at least 10,000 nm. The second lateral dimension may be within a range defined by any two of the preceding values. In some instances, each individually addressable locations may have or be coupled to a binder, as described herein, to immobilize a analyte thereto. In some instances, only a fraction of the individually addressable locations may have or be coupled to a binder. In some instances, an individually addressable location may have or be coupled to a plurality of binders to immobilize an analyte thereto.

The analytes bound to the individually addressable locations may include, but are not limited to, molecules, cells, organisms, nucleic acid molecules, nucleic acid colonies, beads, clusters, polonies, or DNA nanoballs. The bound analytes may be immobilized to the array in a regular, patterned, periodic, random, or pseudo-random configuration, or any other spatial arrangement.

While examples of the present disclosure describe the processing and/or detection of samples and analytes immobilized to individually addressable locations on a substrate, the systems, devices, and methods described herein also allows for detection of the substrate itself (without any samples and/or analytes disposed thereon).

The substrate may be configured to move with respect to the plate. Such motion may be facilitated by one or more actuators or other devices (e.g., gears, stages, actuators, discs, pulleys, motors, etc.). Such actuators and devices may be mechanically connected to the substrate directly or indirectly via intermediary components. Such actuators and devices may be automated. Alternatively or in addition, the actuators and devices may receive manual input. The substrate may be configured to move at any speed that allows for detection. In some instances, or rotational motion, the axis of rotation may be an axis through the center of the substrate. The axis may be an off-center axis. For instance, the substrate may be affixed to a chuck (such as a vacuum chuck). The substrate may be configured to rotate with a rotational velocity of at least 1 revolution per minute (rpm), at least 2 rpm, at least 5 rpm, at least 10 rpm, at least 20 rpm, at least 50 rpm, at least 100 rpm, at least 200 rpm, at least 500 rpm, at least 1,000 rpm, at least 2,000 rpm, at least 5,000 rpm, or at least 10,000 rpm. The substrate may be configured to rotate with a rotational velocity that is within a range defined by any two of the preceding values. The substrate may be configured to rotate with different rotational velocities during different operations described herein. The substrate may be configured to rotate with a rotational velocity that varies according to a time-dependent function, such as a ramp, sinusoid, pulse, or other function or combination of functions. The time-varying function may be periodic or aperiodic.

The fluid barriers provided herein may provide zero friction or low friction relative motion between the substrate and the detector. There may be no mechanical contact between the plate (coupled to the detector) and the chamber (coupled to the substrate).

Detectors (e.g., 101, 1110) of the present disclosure may include devices that are capable of detecting a signal. For example, the signal can be a signal indicative of the presence or absence of one or more components (e.g., incorporated nucleotides, fluorescent labels, electronic signals, etc.) and/or a signal indicative of a change of state in one or more components. The detector may detect multiple signals. The signal or multiple signals may be detected in real-time, prior to, during (or substantially during), or subsequent to a reaction, such as a sequencing reaction. In some cases, a detector can include optical and/or electronic components that can detect signals. A detector may implement one or more detection methods. Non-limiting examples of detection methods include optical detection, spectroscopic detection, electrostatic detection, electrochemical detection, acoustic detection, magnetic detection, and the like. Optical detection methods include, but are not limited to, light absorption, ultraviolet-visible (UV-vis) light absorption, infrared light absorption, light scattering, Rayleigh scattering, Raman scattering, surface-enhanced Raman scattering, Mie scattering, fluorescence, luminescence, and phosphorescence. Spectroscopic detection methods include, but are not limited to, mass spectrometry, nuclear magnetic resonance (NMR) spectroscopy, and infrared spectroscopy. Electrostatic detection methods include, but are not limited to, gel based techniques, such as, for example, gel electrophoresis. Electrochemical detection methods include, but are not limited to, electrochemical detection of amplified product after high-performance liquid chromatography separation of the amplified products.

A detectable signal, such as an optical signal (e.g., fluorescent signal), may be generated upon reaction an analyte and another component (e.g., a probe). For example, the signal may originate from the probe and/or the analyte. The detectable signal may be indicative of a reaction or interaction between the probe and the analyte. The detectable signal may be a non-optical signal. For example, the detectable signal may be an electronic signal. The detectable signal may be detected by one or more sensors. For example, an optical signal may be detected via one or more optical detectors in an optical detection scheme described elsewhere herein. The signal may be detected during motion of the substrate. The signal may be detected following termination of the motion. In some instances, after the detection, the signal may be muted, such as by cleaving a label from the probe and/or the analyte, and/or modifying the probe and/or the analyte. Such cleaving and/or modification may be effected by one or more stimuli, such as exposure to a chemical, an enzyme, light (e.g., ultraviolet light), or temperature change (e.g., heat). In some instances, the signal may otherwise become undetectable by deactivating or changing the mode (e.g., detection wavelength) of the one or more sensors, or terminating or reversing an excitation of the signal. In some instances, detection of a signal may comprise capturing an image or generating a digital output (e.g., between different images).

The detectors may be capable of continuous area scanning, during continuous linear motion and/or a continuous non-linear (e.g., rotational) motion between the sample and the substrate. For example, the detectors can scan a substrate or array along a linear or substantially linear path. Alternatively or in addition, the detectors may scan along a non-linear path, including in rings, spirals, or arcs on a rotating substrate. The detector may be a continuous area scanning detector. A continuous area scanning detector may comprise an imaging array sensor capable of continuous integration over a scanning area wherein the scanning is electronically synchronized to the image of an object in relative motion. A continuous area scanning detector may comprise a time delay and integration (TDI) charge coupled device (CCD), Hybrid TDI, and/or complementary metal oxide semiconductor (CMOS) pseudo TDI.

For rotational scan paths, the scanning direction may be substantially θ in an (R, θ) coordinate system in which the object rotation motion is in a θ direction. Across any field of view on the object (substrate) imaged by a scanning system, the apparent velocity may vary with the radial position (R) of the field point on the object as $$R\frac{d\theta}{dt}.$$

continuous area scanning detectors may scan at the same rate for all image positions and therefore may not be able to operate at the correct scan rate for all imaged points in a curved (or arcuate or non-linear) scan. Therefore the scan may be corrupted by velocity blur for imaged field points moving at a velocity different than the scan velocity. Continuous rotational area scanning may comprise an optical detection system or method that makes algorithmic, optical, and/or electronic corrections to substantially compensate for this tangential velocity blur, thereby reducing this scanning aberration. For example, the compensation is accomplished algorithmically by using an image processing algorithm that deconvolves differential velocity blur at various image positions corresponding to different radii on the rotating substrate to compensate for differential velocity blur. In another example, the compensation is accomplished by using an anamorphic magnification gradient. This may serve to magnify the substrate in one axis (anamorphic magnification) by different amounts at two or more substrate positions transverse to the scan direction. The anamorphic magnification gradient may modify the imaged velocities of the two or more positions to be substantially equal thereby compensating for tangential velocity differences of the two positions on the substrate. This compensation may be adjustable to account for different velocity gradients across the field of view at different radii on the substrate. In some instances, the imaging field of view may be segmented into two or more regions, each of which can be electronically controlled to scan at a different rate. These rates may be adjusted to the mean projected object velocity within each region. The regions may be optically defined using one or more beam splitters or one or more mirrors. The two or more regions may be directed to two or more detectors. The regions may be defined as segments of a single detector.

The systems, devices, and methods described herein may have particular biological applications. In an example, the fluid barrier systems may be used in nucleic acid sequencing applications. A sample environment may be provided within a chamber having a substrate comprising an array. A plurality of nucleic acid molecules may be immobilized to individually addressable locations in the array. A solution of labeled nucleotides may be dispensed to the substrate under conditions sufficient to allow incorporation of at least a subset of the labeled nucleotides into at least a subset of the plurality of nucleic acid molecules, if appropriate (e.g., labeled nucleotides are complementary to an open position in the nucleic acid molecules), and the unincorporated nucleotides washed with a washing solution. The sample environment, including temperature, pressure, and/or humidity, may be maintained in accordance with the particular samples (e.g., nucleic acid molecules) used and/or processing (e.g., incorporation reactions) carried out in the sample environment. Then, while implementing the fluid barriers and thereby maintaining the sample environment conditions, a detector protruding through a plate into the sample environment, configured as described elsewhere herein, may detect one or more detectable signals from the incorporated labeled nucleotides from the individually addressable locations in the array during relative motion of the detector and the substrate. For example, the substrate may be moved relative to the detector such as to allow the detector detects all individually addressable locations in (or a desired sub-area of) the substrate. In some instances, the substrate may undergo a rotational motion and a then a linear motion, in repeated cycles, such that after each rotational motion, the detector is able to scan an annular ring, and after each linear motion, the detector is positioned to scan another annular ring at a different radius from a center of the substrate. Alternatively or in addition, the substrate may undergo only rotational motion. Alternatively or in addition, the substrate may undergo only linear motion.

The fluid barriers maintained during the detection may provide barriers between the controlled sample environment and the external environment, and allow for low friction or zero friction relative motion between the detector and the sample, while maintaining a controlled sample environment. Beneficially, such barriers may allow for continuous scanning in a 100% or substantially 100% relative humidity environment. The barriers may prevent humidity from escaping the sample environment, which when escaped can condense and affect (e.g., corrode, foul, etc.) sensitive equipment, such as the optics. Furthermore, the barriers may prevent contaminants from the external environment from entering the sample environment, which may affect the fluidics and/or detection (e.g., imaging).

As will be appreciated, the systems, devices, and methods described herein may also have non-biological applications, such as for analyzing non-biological samples.

Computer Systems

Figure 5:
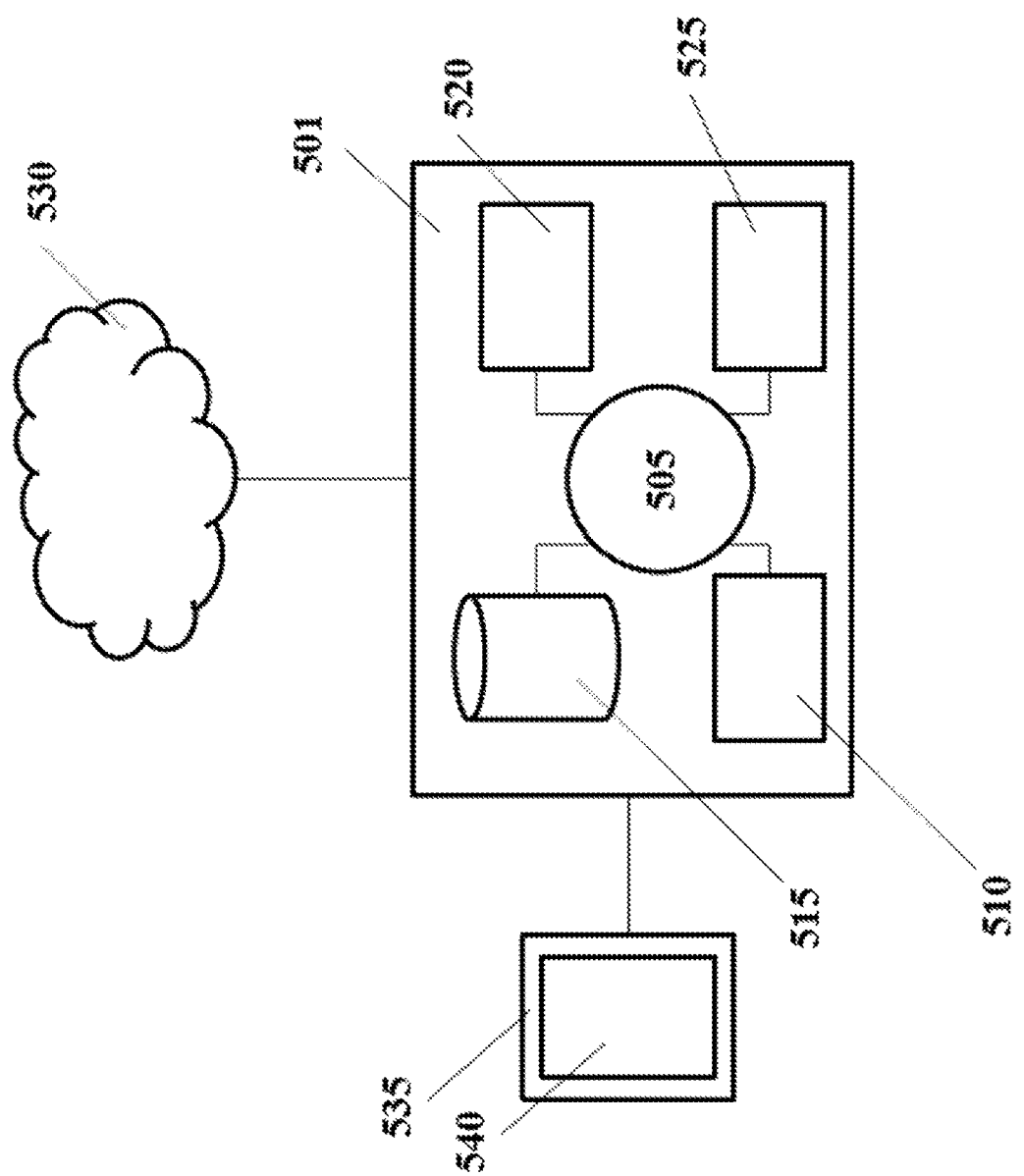
FIG. 5 shows a computer system that is programmed or otherwise configured to implement methods provided herein.

The present disclosure provides computer control systems that are programmed to implement methods of the disclosure. FIG. 5 shows a computer system 501 that is programmed or otherwise configured to process and/or detect a sample. The computer system 501 can regulate various aspects of methods and systems of the present disclosure. For example, the computer system 501 may comprise, or be, a controller configured to communicate with the fluid flow unit, actuators, and/or detectors of the systems described herein.

The computer system 501 includes a central processing unit (CPU, also "processor" and "computer processor" herein) 505, which can be a single core or multi core processor, or a plurality of processors for parallel processing. The computer system 501 also includes memory or memory location 510 (e.g., random-access memory, read-only memory, flash memory), electronic storage unit 515 (e.g., hard disk), communication interface 520 (e.g., network adapter) for communicating with one or more other systems, and peripheral devices 525, such as cache, other memory, data storage and/or electronic display adapters. The memory 510, storage unit 515, interface 520 and peripheral devices 525 are in communication with the CPU 505 through a communication bus (solid lines), such as a motherboard. The storage unit 515 can be a data storage unit (or data repository) for storing data. The computer system 501 can be operatively coupled to a computer network ("network") 530 with the aid of the communication interface 520. The network 530 can be the Internet, an internet and/or extranet, or an intranet and/or extranet that is in communication with the Internet. The network 530 in some cases is a telecommunication and/or data network. The network 530 can include one or more computer servers, which can enable distributed computing, such as cloud computing. The network 530, in some cases with the aid of the computer system 501, can implement a peer-to-peer network, which may enable devices coupled to the computer system 501 to behave as a client or a server.

The CPU 505 can execute a sequence of machine-readable instructions, which can be embodied in a program or software. The instructions may be stored in a memory location, such as the memory 510. The instructions can be directed to the CPU 505, which can subsequently program or otherwise configure the CPU 505 to implement methods of the present disclosure. Examples of operations performed by the CPU 505 can include fetch, decode, execute, and writeback.

The CPU 505 can be part of a circuit, such as an integrated circuit. One or more other components of the system 501 can be included in the circuit. In some cases, the circuit is an application specific integrated circuit (ASIC).

The storage unit 515 can store files, such as drivers, libraries and saved programs. The storage unit 515 can store user data, e.g., user preferences and user programs. The computer system 501 in some cases can include one or more additional data storage units that are external to the computer system 501, such as located on a remote server that is in communication with the computer system 501 through an intranet or the Internet.

The computer system 501 can communicate with one or more remote computer systems through the network 530. For instance, the computer system 501 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 501 via the network 530.

Methods as described herein can be implemented by way of machine (e.g., computer processor) executable code stored on an electronic storage location of the computer system 501, such as, for example, on the memory 510 or electronic storage unit 515. The machine executable or machine readable code can be provided in the form of software. During use, the code can be executed by the processor 505. In some cases, the code can be retrieved from the storage unit 515 and stored on the memory 510 for ready access by the processor 505. In some situations, the electronic storage unit 515 can be precluded, and machine-executable instructions are stored on memory 510.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 501 can include or be in communication with an electronic display 535 that comprises a user interface (UI) 540 for providing, for example, detection results to a user. The UI may further present a console for configuring the fluid barrier systems, and/or components thereof (e.g., pressure-altering apparatus, environmental units, detectors, immersion enclosure, motion of detectors, motion of plates, motion of containers, motion of substrates, sample processing, etc.) of the present disclosure. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 505.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for processing a biological analyte, comprising:
    (a) providing a barrier between a first region and a second region, wherein said first region comprises a substrate having said biological analyte immobilized adjacent thereto, wherein said barrier maintains said first region at a first atmosphere that is different than a second atmosphere of said second region; and
    (b) using a detector at least partially contained in said first region to detect one or more signals or changes thereof from said biological analyte while (i) said detector is undergoing translational motion relative to said substrate, wherein said substrate and said detector are not in direct mechanical contact, and (ii) said first region is maintained at said first atmosphere that is different than said second atmosphere of said second region.

2. The method of claim 1, wherein a portion of said barrier comprises fluid in bulk motion.

3. The method of claim 2, wherein said portion of said barrier comprises a partial vacuum.

4. The method of claim 2, wherein said portion of said barrier comprises fluid from said first region, said second region, or both.

5. The method of claim 1, wherein said first atmosphere is maintained at a first humidity that is different than a second humidity of said second atmosphere.

6. The method of claim 5, wherein said first atmosphere has a relative humidity greater than 90%.

7. The method of claim 1, wherein said detector is an optical detector, and wherein said one or more signals are one or more optical signals or signal changes.

8. The method of claim 1, wherein said barrier comprises a first solid component and a second solid component, wherein said first solid component and said second solid component are not in direct mechanical contact, and wherein said first solid component is movable relative to said second solid component.

9. The method of claim 8, wherein a portion of said barrier comprises fluid in bulk motion, and wherein said portion is disposed between said first solid component and said second solid component.

10. The method of claim 8, wherein said detector is fixed relative to said first solid component and wherein said substrate is translationally fixed relative to said second solid component.

11. The method of claim 8, wherein said substrate is rotatable relative to said second solid component.

12. The method of claim 8, wherein a first part of said first solid component is provided between said first region and said second region, and wherein a second part of said first solid component is provided between said second region and a third region to form part of another barrier configured to maintain said third region at a third atmosphere that is independent of said first atmosphere and said second atmosphere, wherein a portion of said another barrier comprises fluid in bulk motion, and wherein said third region is movable relative to said first solid component independent of said first region.

13. The method of claim 1, wherein said second atmosphere is a room atmosphere or an ambient atmosphere.

14. The method of claim 1, wherein a first part of said detector is in said first region and a second part of said detector is in said second region.

15. The method of claim 14, wherein said first part of said detector comprises an optical imaging objective at least partially immersed in an immersion fluid in contact with said substrate in said first region.

16. The method of claim 1, wherein said biological analyte is a nucleic acid molecule, and further comprising, based at least in part on said one or more signals or changes thereof, identifying a sequence of said nucleic acid molecule or derivative thereof.

17. A method for processing a biological analyte, comprising:
(a) providing a barrier between a first region and a second region, wherein said first region comprises said biological analyte, wherein said barrier maintains said first region at a first atmosphere that is different than a second atmosphere of said second region, wherein a portion of said barrier comprises fluid in bulk motion; and
(b) using a detector at least partially contained in said first region to detect one or more signals or change thereof from said biological analyte while said first region is maintained at said first atmosphere that is different than said second atmosphere of said second region.

18. The method of claim 17, wherein said portion of said barrier comprises fluid from said first region, said second region, or both.

19. The method of claim 17, wherein said first atmosphere is maintained at a first humidity that is different than a second humidity of said second atmosphere.

20. The method of claim 19, wherein said first atmosphere has a relative humidity greater than 90%.

21. The method of claim 17, wherein (b) comprises moving said detector relative to said biological analyte while detecting.

22. The method of claim 17, wherein said detector is an optical detector, and wherein said one or more signals or change thereof are one or more optical signals or change thereof.

23. The method of claim 17, wherein said barrier comprises a first solid component and a second solid component, wherein said first solid component and said second solid component are not in mechanical contact, and wherein said first solid component is movable relative to said second solid component.

24. The method of claim 23, wherein said portion of said barrier comprising said fluid is disposed between said first solid component and said second solid component.

25. The method of claim 23, wherein said detector is fixed relative to said first solid component and wherein said biological analyte is translationally fixed relative to said second solid component.

26. The method of claim 23, wherein a first part of said first solid component is provided between said first region and said second region, and wherein a second part of said first solid component is provided between said second region and a third region to form part of another barrier configured to maintain said third region at a third atmosphere that is independent of said first atmosphere and said second atmosphere, wherein a portion of said another barrier comprises fluid, and wherein said third region is movable relative to said first solid component independent of said first region.

27. The method of claim 17, wherein said second atmosphere is a room atmosphere or an ambient atmosphere.

28. The method of claim 17, wherein a first part of said detector is in said first region and a second part of said detector is in said second region.

29. The method of claim 28, wherein said first part of said detector comprises an optical imaging objective at least partially immersed in an immersion fluid in contact with said biological analyte in said first region.

30. The method of claim 17, wherein said biological analyte is a nucleic acid molecule, and further comprising, based at least in part on said one or more signals or signal changes, identifying a sequence of said nucleic acid molecule or derivative thereof.

* * * * *